United States Patent [19]

Cooper et al.

[11] Patent Number: 4,599,219

[45] Date of Patent: Jul. 8, 1986

[54] COAGULATION DETECTION BY PLUNGER SENSING TECHNIQUE

[75] Inventors: Daniel Cooper, Parker; Jacqueline J. Jackson, Denver, both of Colo.

[73] Assignee: Hemotec, Inc., Englewood, Colo.

[21] Appl. No.: 434,718

[22] Filed: Oct. 15, 1982

[51] Int. Cl.[4] ............................................ G01N 33/86
[52] U.S. Cl. ........................................ 422/61; 73/57; 73/64.1; 356/39; 422/58; 422/73; 422/102; 436/43; 436/69; 436/165
[58] Field of Search ................................ 422/100-103, 422/57, 58, 61, 73, 119, 44; 436/69, 165, 809, 43; 73/64.1, 57; 435/13; 210/918

[56] References Cited

U.S. PATENT DOCUMENTS

| | | | |
|---|---|---|---|
| 4,036,231 | 7/1977 | Dodge et al. | 128/276 |
| 4,058,367 | 11/1977 | Gilford | 422/63 |
| 4,074,971 | 2/1978 | Braun et al. | 436/69 |
| 4,129,131 | 12/1978 | Naftulin | 128/276 |
| 4,197,735 | 4/1980 | Munzer et al. | 422/100 |
| 4,210,623 | 6/1980 | Breno et al. | 422/101 |
| 4,332,264 | 6/1982 | Gortz et al. | 134/57 R |
| 4,391,780 | 7/1983 | Boris | 422/102 |

Primary Examiner—Arnold Turk
Attorney, Agent, or Firm—John R. Ley

[57] ABSTRACT

Coagulation is detected in a fluid sample contained in either a gas flow cartridge or a plunger sensor cartridge, either one of which may be inserted in an actuator mechanism which has the capability of acting on either type of cartridge. Coagulation is detected in the gas flow cartridge by optically sensing the accumulation of coagulating liquid in a foam member at the top of the reaction chamber. In the plunger sensor cartridge, a plunger assembly is raised and released to descend through the sample of liquid in the bottom of the reaction chamber. The plunger assembly descends more slowly upon an increase in the viscosity of the fluid sample due to coagulation. Both cartridges include a lower reagent chamber, an upper reaction chamber, and means initially sealing and thereafter communicating the contents from the reagent chamber to the reaction chamber. The actuator mechanism includes means for delivering the flow of gas to the gas flow cartridge and means for reciprocating the plunger assembly in the plunger sensor cartridge.

68 Claims, 32 Drawing Figures

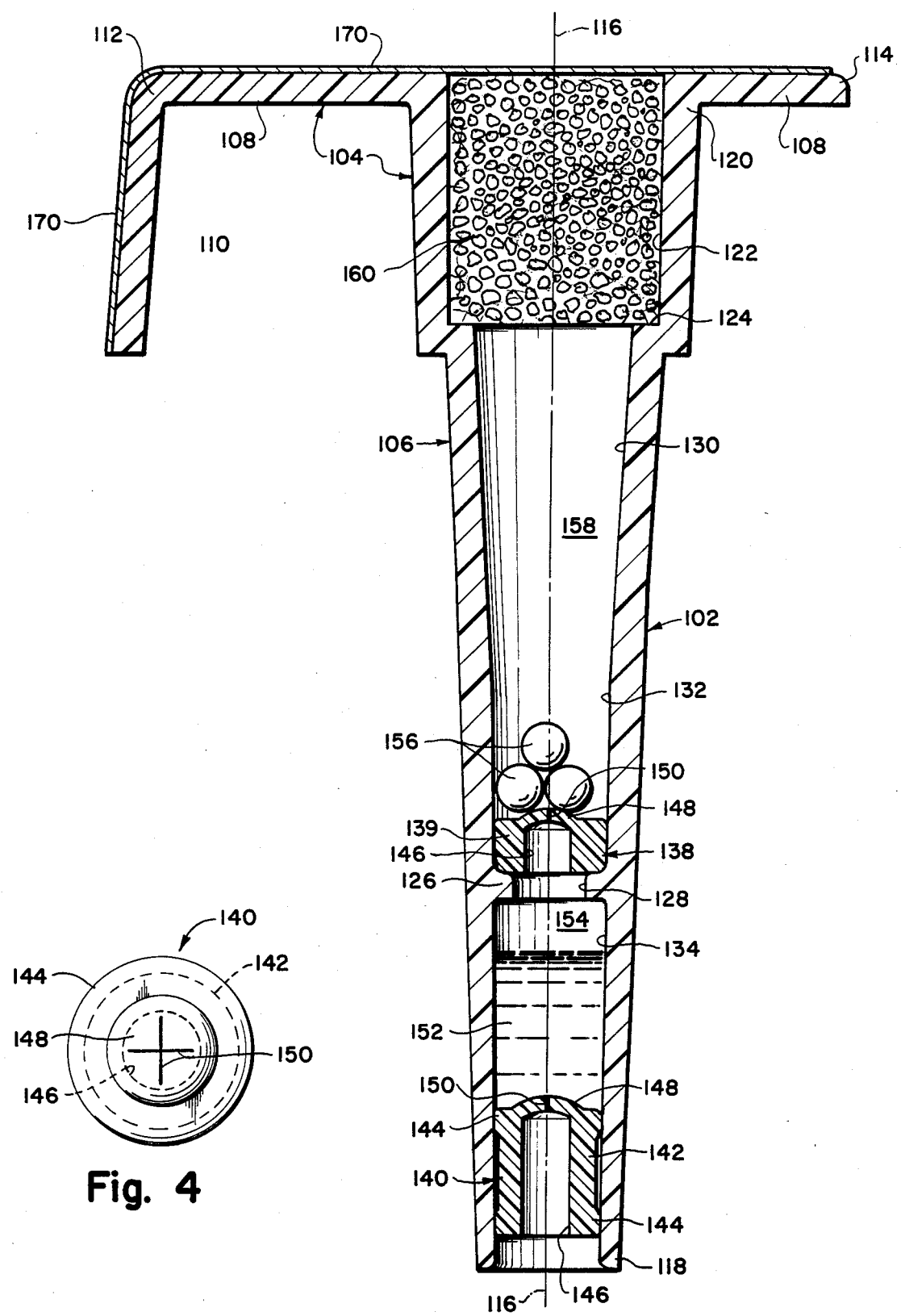

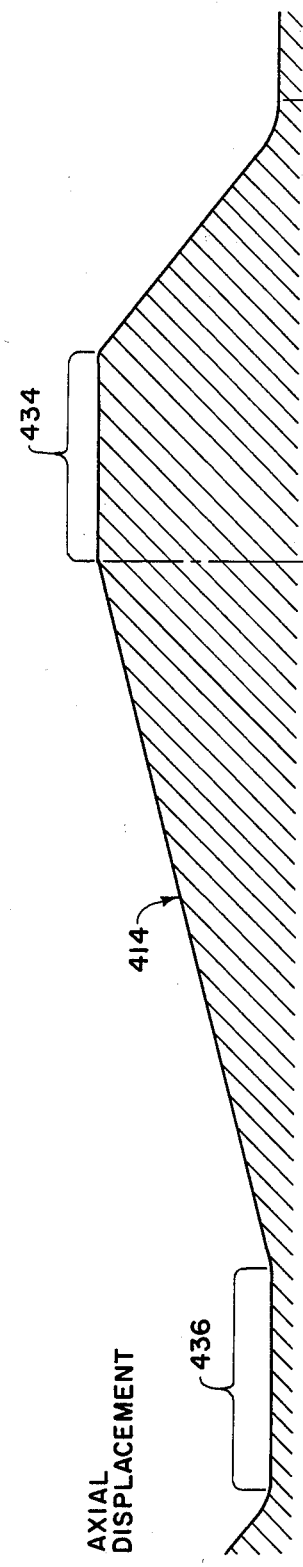
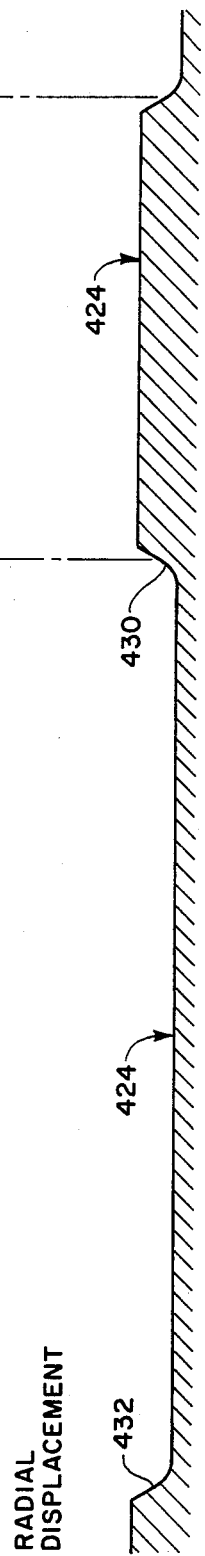
Fig. 20A
Fig. 20B

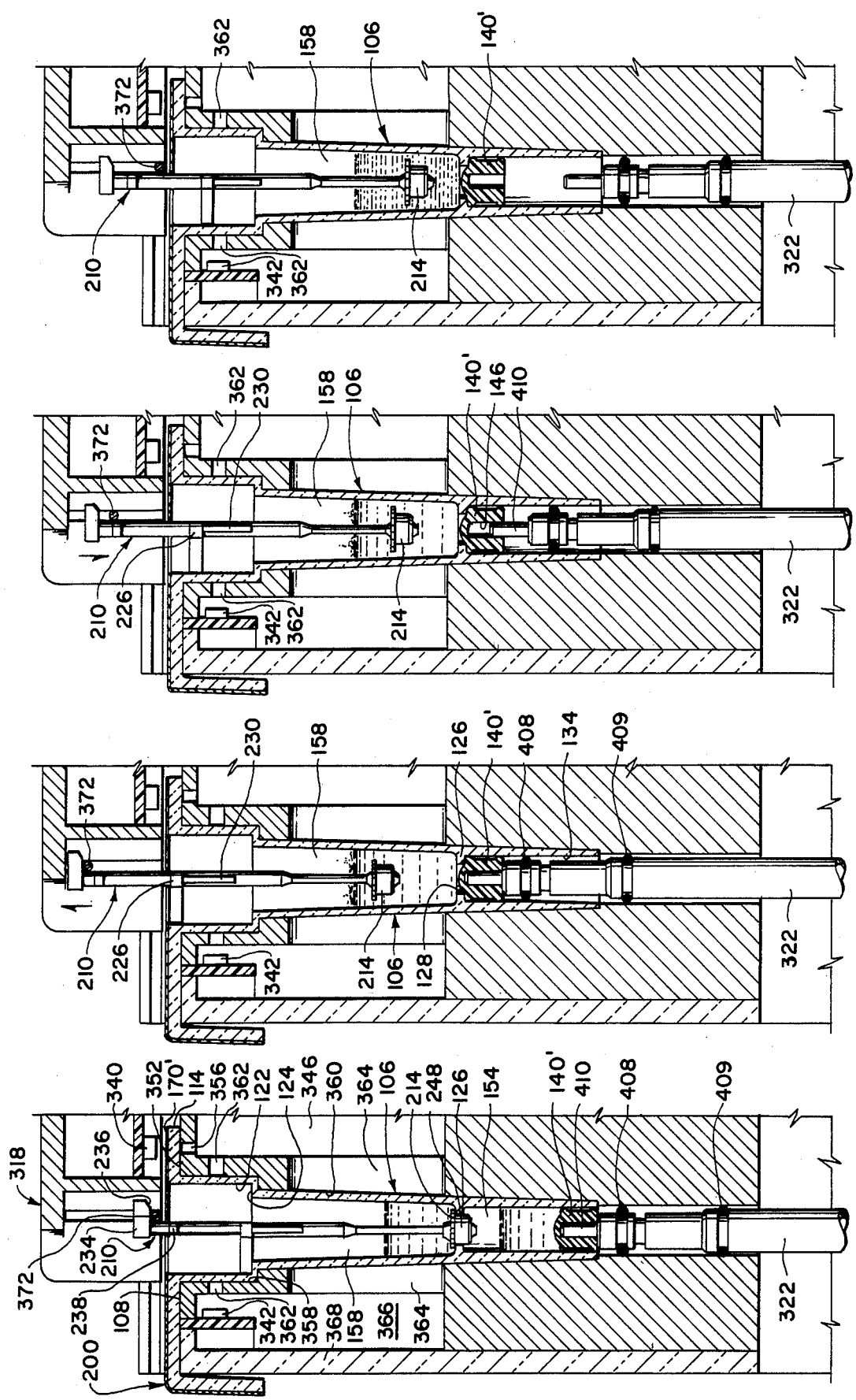

COAGULATION DETECTION BY PLUNGER SENSING TECHNIQUE

This invention pertains to measuring and detecting coagulation and coagulation-related factors in fluids, particularly human blood. More particularly, the present invention relates to improvements in measuring and detecting coagulation and coagulation-related factors in human blood by different types of analytical tests, including clotting time tests, response to anticoagulant tests (dose response tests), and titration tests, on a selective basis. Even further still, the present invention relates to improvements in accurately and reliably detecting coagulation in blood which has been subjected to low dose heparin or anticoagulant therapy.

There exist a number of different apparatus and methods for measuring and determining coagulation and coagulation-related factors of blood. Although previous manual techniques for accomplishing all of the coagulation and coagulation-related analytical tests are available, such manual tests are generally subject to variable results and inaccuracies because individual variations in test procedures are introduced by the technicians conducting the tests. Furthermore, manual analytical tests can require relatively long periods of time to complete the tests. It is, therefore, recognized as desirable to provide apparatus which can reliably and consistently execute analytical tests under consistent, reproducible conditions.

The test results available from many of the previous machines do not reliably relate to the test results available from recognized and accepted manual analytical laboratory techniques. Because physicians are accustomed to test results derived from recognized manual laboratory techniques, such machines are not regarded as universally reliable.

Examples of apparatus and methods which do obtain reliable test results in certain types of coagulation detection analytical tests are U.S. Pat. Nos. 4,000,972 and 4,074,971, both assigned to the assignee of the present invention. The success of these methods and apparatus have been primarily confined to situations where anticoagulant or heparin has been administered in relatively high therapeutic medical dosages of between 3.5 and 7.0 units of heparin per milliliter of blood, for example. An example of a therapeutic medical dosage is a typical cardiovascular surgical situation such as a pulmonary bypass surgical operation. In such circumstances, an extracorporeal bypass circuit and pump are employed to assure the continued flow of blood in the patient during the surgical procedure. Relatively high therapeutic dosages of anticoagulant are administered to prevent the blood from clotting in the bypass circuit and pump and in the body as a result of environmental changes brought on by the surgery. In such situations, the dosage of anticoagulant administered must be sufficient only to extend the clotting time of the blood within a preestablished and relatively wide range. So long as the clotting time of the blood remains in this relatively wide range, the patient is regarded as relatively free from danger.

Low dose heparin or anticoagulant therapy normally requires the clotting time of the blood to be slightly extended and confined within a relatively narrow range. Low dose anticoagulant treatment usually involves administering between 0.1 and 1.0 units of anticoagulant or heparin per milliliter of blood. Low dose heparin therapy is used in a wide variety of clinical applications, such as prophylaxis of post-operative deep vein thromboembolism and pulmonary embolus; hemodialysis; following acute myocardial infarction; disseminated intravascular coagulation; in obstetrical cases where anticoagulant transport across the placenta is undesirable; in surgery for malignant disease; in hip surgery; for shock; septicemia, purpura fulminans; septic abortion; abruptio placentae; amniotic fluid embolism; burns; following major surgery; organ transplantation; glomerulonephritis; hemolytic uremic syndrome; thrombotic-thrombocytopenic purpura; retained dead fetus syndrome; and giant hemangioma. Administration of heparin is most effective when given by constant infusion; however, intermittent injections, subcutaneous injections and inhalation have also been used.

The response of heparin or anticoagulant dosage in humans is highly individualized and is, to some extent, influenced by the underlying disease processes. Dosage is largely empirical and is established in many instances by protocol. Monitoring of heparin therapy is essential, especially in view of varying responses and actual resistance of the patient. Dose response tests obtain information with respect to increases in clotting times as a result of administering different doses of anticoagulant to the blood. Once data points are established by this test, a curve or linear approximation can be derived which relates the amount of heparin administered to achieve a desired extended clotting time. Dose response tests are important in anticipating the variability of individual responses. A clotting time or activated clotting time analytical test is important in determining whether the anticoagulated blood has reached the desired safe limits of extended clotting time. A heparin/protamine or coagulant/neutralent titration analytical test provides a quantitative determination of the heparin concentration.

It is, therefore, desirable and necessary to have the ability to conduct each of the different types of coagulation related analytical tests during clinical and surgical procedures. The ability to conduct each of the analytical tests on a relatively rapid and alternating basis is important, depending on the state of the clinical or surgical procedure. At the present time, there is no known single apparatus or method which is capable of conducting all the different types of coagulation and coagulation-related analytical tests on an alternatively selectable and rapid basis with automated consistency on blood or fluid treated with low doses of anticoagulant to achieve rapid, reliable and reproducible analytical test results.

SUMMARY

The apparatus of the present invention is capable of conducting clotting time tests, dose response tests and titration tests on a selectively alternative basis on samples of blood or fluid which have been subjected to low dose anticoagulant therapy. Furthermore, the particular apparatus employed in each analytical test is structurally and operatively arranged to achieve the most reliable test results from that particular analytical test. The test results are highly reliable in the sense that they directly correlate to the laboratory tests which are the established norms with which physicians are familiar, follow the same or similar limitations or constraints imposed by the established laboratory tests, and eliminate discrepancies that may be introduced by individual procedures of laboratory technicians. The test results are highly accurate because the detection of coagulation is achieved by methods and apparatus which are highly sensitive and responsive to conditions indicative of coagulation in samples of blood or fluid which have been subjected to low dose anticoagulant therapy. The test results are conducted relatively rapidly, and the results and any calculations based on the results are presented almost immediately after termination of the tests. Reliable test results are achieved on human blood or other fluid which has been treated with low doses of anticoagulant, i.e., between 0.1 and 1.0 units of heparin per milliliter.

In accordance with its broad aspects, the present invention is directed toward an apparatus capable of conducting clotting time tests, dose response tests and titration tests. The coagulation-related analytical tests are carried out in a gas flow cartridge and/or a plunger sensor cartridge. Preferably, clotting time tests and dose response tests will be conducted with the gas flow cartridge because that cartridge offers advantages in statistical reliability for those types of tests. Titration tests and dose response tests where the sample of fluid or blood is essentially neutralized will be conducted using the plunger sensor cartridge because that cartridge offers better statistical reliability for those types of tests. The tests are conducted by a machine which operates in conjunction with either one or both of the cartridges. The machine includes features and apparatus operable to conduct any one of the three types of tests with either one of the cartridges. The machine recognizes the types of cartridge in which the test is to be conducted and conducts the test procedure accordingly. Both cartridges have certain elements in common, and each cartridge has individually different operational elements. The individually different operational elements of the different types of cartridges are arranged to avoid operational interference with one another when the cartridge is inserted into an actuator mechanism of the machine. The actuator mechanism includes means adapted to operate directly on the operational elements of either type of cartridge to conduct the analytical tests. The operating procedure of the actuator mechanism is established for both types of cartridges by an operating system which includes a microprocessor computer.

The actuator mechanism of the machine delivers a flow of gas to the gas flow cartridge. Bubbles created by the gas carry the liquid fluid from the pool of fluid inserted in the cartridge upon which the test is conducted. Coagulation is optically detected upon the accumulation of coagulated fluid from the bubbles on a foam element of the gas flow cartridge. The plunger sensor cartridge includes a plunger assembly which is reciprocated within the pool of fluid in the cartridge. The actuator mechanism lifts the plunger assembly and releases it to allow it to descend by the force of gravity resisted only by the viscosity of the fluid in the cartridge. When the viscosity increases to a predetermined extent, thereby indicating coagulation is occurring within the fluid, the descent rate of the plunger therethrough is slowed. The descent of the plunger assembly is optically sensed. Both cartridges include a partition defining the open interior of the tube-like member into an upper reaction chamber where the analytical test is carried out and a lower reagent chamber which contains a reagent to be mixed with the pool of liquid in the reaction chamber when the test commences. A passageway extends through the partition, and means separate from the partition initially seals the passageway and selectively opens the passageway to fluid communication between the reaction and reagent chambers in preparation for the test. Both cartridges include a plug member which operatively seals a lower reagent chamber. The contents of the lower reagent chamber are forced into a reaction chamber where the pool of fluid is tested for coagulation. Elements of the actuator assembly force the plug member upwardly to transfer the reagent chamber contents into the reaction chamber.

The nature and details of the present invention can be more completely understood by reference to the following description of a preferred embodiment taken in conjunction with the drawings, and from the appended claims.

DRAWINGS

FIG. 3 is an enlarged vertical section view through one of the test cells of the gas flow cartridge, taken in the plane of line 3—3 shown in FIG. 2.

FIG. 4 is a top plan view of a plug member shown in FIG. 3.

FIGS. 20A and 20B are graphs of cam contours of a cam wheel of the actuator mechanism shown in FIG. 16, with each cam contour shown relative to a common operational position.

FIGS. 24A, 24B, 24C and 24D are sequential views of the plunger sensor cartridge shown in FIG. 5 in the actuator mechanism shown in FIG. 15, illustrating use in a coagulation detection analytical test.

DETAILED DESCRIPTION

INTRODUCTION

Figure 1:
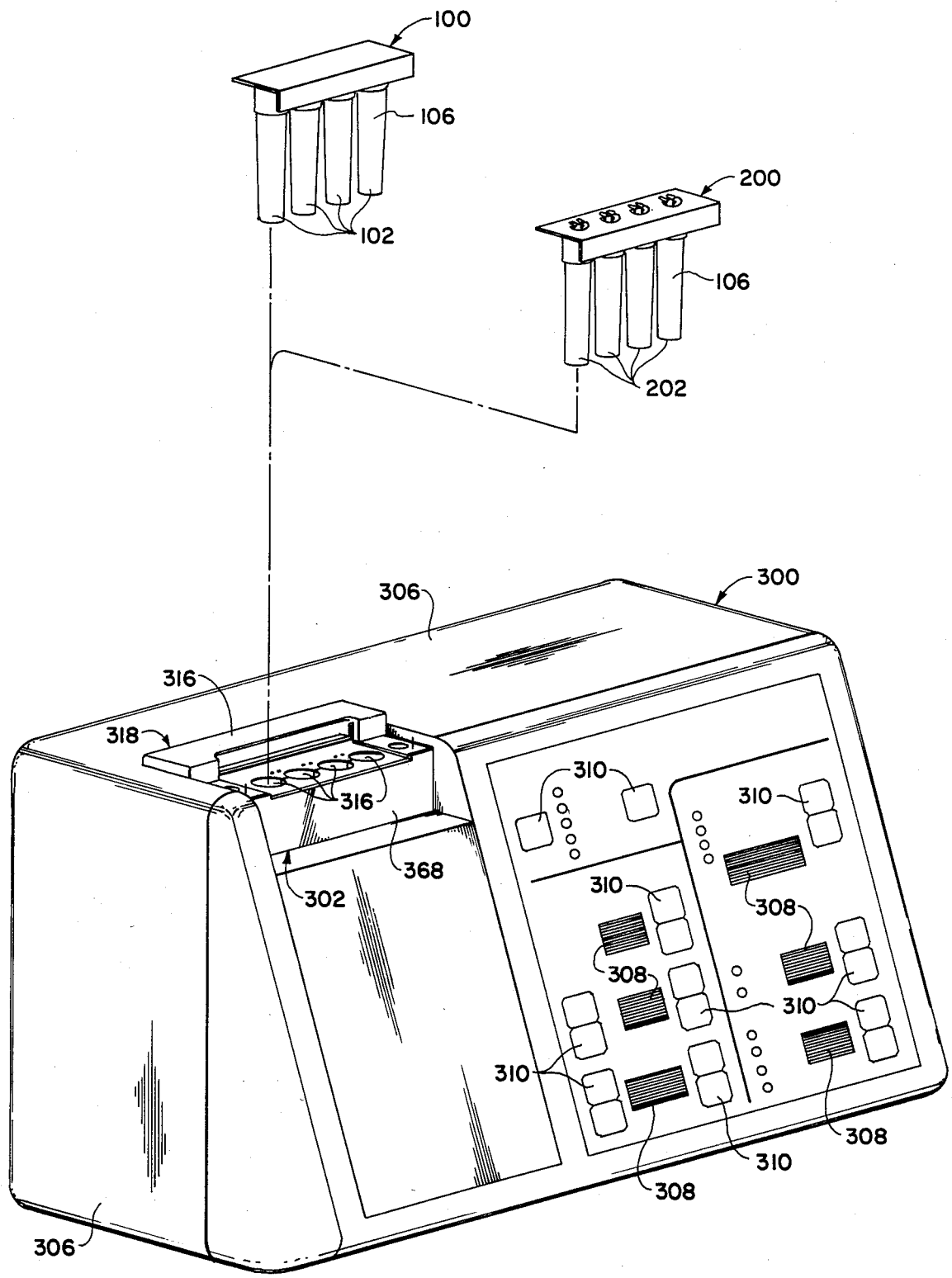
FIG. 1 is a perspective view of a gas flow cartridge, a plunger sensor cartridge, and a machine with which the cartridges are used on selectively alternate basis, all of which comprises apparatus for measuring and detecting coagulation and coagulation-related factors in fluids, in accordance with the present invention.

To conduct coagulation detection analytical tests, a gas flow cartridge 100 and a plunger sensor cartridge 200 are used, preferably on a selective basis, with a machine 300, as shown in FIG. 1. The machine 300 and one or both of the cartridges 100 and 200 comprise apparatus for detecting coagulation and coagulation-related factors in fluids, such as human blood, and measuring the elapsed time for coagulation to occur, and deriving and displaying other additional information regarding coagulation and coagulation-related factors of the fluid, and if the fluid is blood, of the patient. Each of the cartridges 100 and 200 include a plurality of test cells 102 and 202, respectively, into which a predetermined quantity or sample of the fluid or blood is introduced. After the fluid is introduced into the test cells of a selected one of the cartridges 100 or 200, the selected cartridge is operatively inserted into the machine 300. The machine 300 operatively conducts an analytical test following a predetermined or programmed operational procedure in accordance with the type of cartridge and the analytical test to be conducted. By use of the cartridges 100 and 200, the machine 300 accurately, quickly and reliably conducts coagulation (clotting) time tests, dose response tests and titration tests on a rapid, reliable and accurate basis.

In general, analytical tests utilizing the flow cartridge 100 proceed with the machine 300 directing a flow of gas upward through each of the test cells 102. The interaction of the gas with the sample of fluid in each test cell creates conditions which allow the machine 300 to detect and measure coagulation and coagulation-related factors. In analytical tests using the plunger sensor cartridge 200, a plunger assembly within each test cell 202 is repeatedly raised and dropped or allowed to descend through a pool of fluid in the test cell. The time for descent of the plunger assembly through the pool of fluid is detected and measured to detect coagulation and coagulation-related factors. The machine 300 contains an actuator mechanism which operates with both types of cartridges for conducting the analytical tests. The machine 300 is further capable of distinguishing between the gas flow cartridge 100 and plunger sensor cartridge 200, and the type of analytical test to be conducted with either type of cartridge, to properly operate with each type of cartridge inserted into the machine.

To obtain high accuracy and reliability from the clotting time, dose response and titration analytical tests, it has been discovered that the gas flow cartridge 100 and plunger sensor cartridge 200 each offer substantial advantages, according to the type of analytical test. Use of the gas flow cartridge 100, it has been discovered, offers more reliable and accurate data in the clotting time and dose response analytical tests. In clotting time and dose response tests, different amounts of reagents are mixed with the samples of fluid or blood in each of the test cells. The statistical scatter of data points on a graph of amount of anticoagulant versus clotting time in both the dose response and clotting time studies is less significant, and hence more accurate, when the gas flow cartridge is used. In titration tests, or in clotting time tests where very little or no anticoagulant is introduced into the fluid or blood sample, the blood or fluid sample is more nearly in its natural uninfluenced state; and the plunger sensor cartridge offers the advantage of being able to mechanically sense or "feel" the initiation of coagulation at elapsed times which are statistically more accurate than can be determined by use of the gas flow cartridge. It appears that relatively high anticoagulant or heparin levels in a blood sample result in such a thin clot that it is difficult with the plunger sensor cartridge to feel or sense the initiation of coagulation or formation of the clot with satisfactory repeatable statistical accuracy. The gas flow cartridge, in this regard, offers better test results and more nearly duplicates the recognized and accepted manual laboratory test methods.

The aspects of the present invention are better appreciated from the following descriptions of the gas flow cartridge 100, the plunger sensor cartridge 200, the machine 300, and their cooperative operation.

Gas Flow Cartridge

Figure 2:
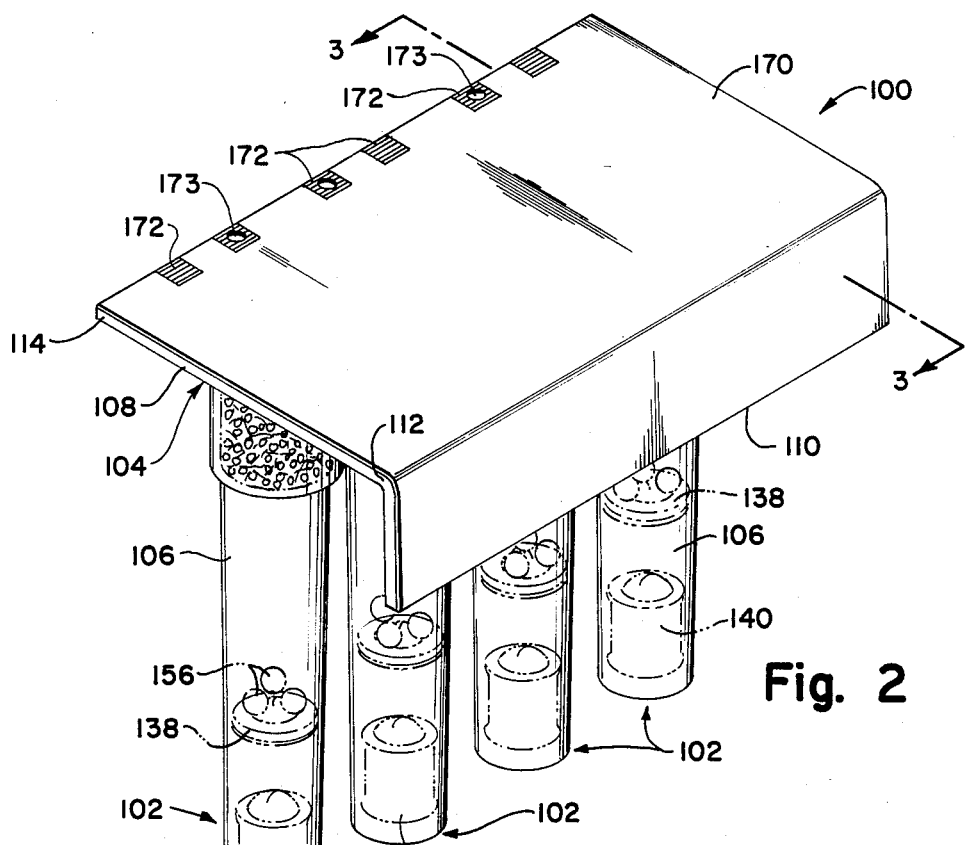
FIG. 2 is an enlarged perspective view of the gas flow cartridge shown in FIG. 1.

The gas flow cartridge 100 is shown in greater detail in FIGS. 2 and 3 and includes a housing 104 preferably formed of integral clear acrylic plastic. Four transversely aligned and vertically open tube-like members 106 extend downward from an upper shelf portion 108 of the housing 104. A lip 110 extends downward from a forward edge 112 of the shelf portion 108. The tube-like members 106 are positioned intermediate the front edge 112 and a rear edge 114 of the shelf portion 108, and are spaced in transverse alignment at equal intervals along the shelf portion 108. Each of the tube-like members 106 has essentially the same predetermined configuration, and its shape is concentric about a center axis 116 through each tube-like member 106.

The tube-like member 106 defines the enclosure of each test cell 102. Each tube-like member 106 has an open lower end 118 and an open upper end 120. The upper end 120 is integrally connected to the shelf portion 108. An initial upper portion of the tube-like member extends downwardly from the upper end 120 and defines an interior, generally cylindrical surface 122. The extent along the axis 116 to which the cylindrical surface 122 extends is approximately the same as that distance which the lip 110 extends downward from the forward edge 114 of the upper shelf portion 108. An annular shoulder 124 extends radially inward at the lower end of the cylindrical surface 122. A partition 126 extends radially inward toward the axis 116 from each tube-like member 106 at a position intermediate the shoulder 124 and the lower end 118. A cylindrical axial passageway 128 extends axially through the partition 126. A downwardly-converging, frustoconical-shaped inner surface 130 extends from the shoulder 124 to a position intermediate the shoulder 124 and the partition 126. A substantially cylindrical surface 132 extends from the lower end of the frustoconical-shaped surface 130 to the partition 126. Another cylindrical surface 134 extends downward from the partition 126. The lower edge of the cylindrical surface 134 is divergently curved radially outward at the lower end 118 of the tube-like member.

An upper plug member 138 and a lower plug member 140, each of which is formed of resilient, flexible material such as Kraton, are frictionally received within the interior opening of the tube member 106 defined by the surfaces 132 and 134, respectively. Both plug members 138 and 140 have rotational concentricity about the axis 116. The upper plug member 138 includes a generally cylindrical main body portion 139. The lower plug member 140 includes a generally cylindrical main body portion 142 from which a pair of ring-like edges 144 protrude outwardly at each axial end of the plug member 140, as is also shown in FIG. 4. A center cylindrical opening 146 extends axially through both main body portions 139 and 142. A upwardly convex-shaped dome portion 148 of uniform thickness extends across the upper axial end of each main body portion 139 and 142 and closes the center opening 146 at its upper end. A pair of crossing diametrical slits 150 extend completely axially through the dome portion 148 at the axis 116 of each plug member. The slits preferably cross one another at right angles. The terminal ends of the slits 150 are slightly radially inwardly spaced from the inner surface of the center opening 146. A coating of a lubricant-like sealant may be applied to the slits 150. The sealant further assures closure of the slits prior to use. The sealant should be non-hydroscopic, have relatively low shear strength to allow the slits 150 to open, have the ability to adhere to the dome portion, and be compliant to move slightly with the dome portion prior to use of the cartridge.

The upper plug member 138 is inserted from the upper end 120 of the tube-like member 106 downwardly along the surface 134 until the lower end of the main body portion 139 contacts and rests on the partition 126. The center opening 146 of the plug member 138 extends upward from the passageway 128 in the partition 126, and the dome portion 148 is spaced above the partition 126 by the axial length of the center opening 146. The cylindrical exterior side walls of the main body portion 139 contact, frictionally engage and seal with the surface 132 of the tube-like member. The main body portion is slightly radially compressed when in contact with the surface 132 to develop sufficient retention force to hold the upper plug member 138 in place during use of the cartridge.

The plug member 140 is inserted from the lower end 118 of the tube-like member 106 upwardly along the surface 134. The edges 144 frictionally engage with, and resiliently seal against, the surface 134 of the tube-like member. The resiliency of the material of the dome portion 148 of both plug members 138 and 140 normally holds the slits 150 in a closed sealed position, thereby preventing the passage of fluid through the slits 150.

The upper plug member 138 is first inserted into the tube-like member 106. Before the lower plug member 140 is inserted into the lower end of the lower center opening 134, a predetermined quantity and type of reagent 152 is inserted into a reagent chamber 154. The reagent chamber 154 is enclosed and defined at the upper end by the upper plug member 138, at the sides by the surface 134, and at the lower end by the lower plug member 140 which is resiliently sealed against the interior surface 134 of the tube-like member. The slits 150 remain closed to confine the reagent 152 to the reagent chamber 154. To insert the reagent 152 into the reagent chamber 154, the housing 104 is inverted from the position shown in FIGS. 2 and 3, and the reagent 152 is added into the reagent chamber. A wire is placed alongside the lower plug member 140 as it is inserted into the lower open end of the tube-like member, and then the wire is removed. The wire deforms the edges 144 to vent air from the reagent chamber as the lower plug member moves into the reagent chamber.

The type and quantity of reagent 152 inserted into the reagent chamber 154 depends on the purpose for which the cartridge 100 is to be used. For dose response tests, heparin will typically be part of the reagent. A different quantity of heparin will be introduced into the reagent chambers of each of the test cells 102 in a single cartridge 100. For titration tests, the reagent could include heparin or protamine, in variable amounts in the reagent chambers of the test cells of the cartridge. For clotting time tests, the same predetermined quantity of activating substance is introduced into each of the reagent chambers in each of the test cells 102.

At least one and preferably three small ball members 156 are inserted into a reaction chamber 158 of the tube-like member 106. The reaction chamber 158 is defined on the sides by the surfaces 130 and 132 and extends axially above the upper plug member 138 to the shoulder 124. The balls 156 are preferably formed of glass. The glass surfaces of the balls 158 react beneficially with the blood, in a manner thought to simulate the glass test tubes and containers in which laboratory tests are typically carried out. For determining coagulation and coagulation-related factors in other types of fluid, the balls may be dispensed with, or they may be constructed from other types of material.

An open-cell foam member 160 is inserted from the upper end 120 into the upper interior opening in the tube-like member 106 defined by the cylindrical surface 122. The foam member 160 is preferably of a right cylindrical configuration, and its axial length is approximately the same as the length between the shoulder 124 and the upper end 120 of the tube-like member 106. The foam member 160 is inserted downwardly until it contacts the shoulder 124, and the lower edge of the foam member extends across the upper margin of the reaction chamber 158. Prior to insertion in the tube-like member, the foam member 160 and its internal structure is coated with a debubbling agent such as silicone. The debubbling agent causes liquid contacting the strand-like or fiber-like internal structure of the foam material 160 to reflux or drain downward and not collect in the interstices in the foam material. Preferably, the foam material is formed of synthetic plastic.

A cover 170 is attached to the upper surface of the shelf portion 108. The cover preferably also extends around and down on the front outer surface of the lip 110. The cover 170 is preferably a single piece of paper and is attached preferably by gluing it around the outer edges of the shelf portion 108, and on the outer front surface of the lip 110. The paper cover 170 contains printed indicia indicative of the type of analytical test to be conducted with the cartridge. The type of test is determined by the type and quantity of reagent 152 present in the reagent chamber 154. Furthermore, printed indicia may also indicate the quantities or strengths of reagent in the reagent chambers. A code 172 is also present on the paper cover 170 on top of the rear edge 114 of the housing 104, as shown in FIG. 2. The code 172 is optically sensed to create signals indicating the type of cartridge, either gas flow or plunger sensor, the type of analytical test to be conducted with the cartridge and, in some instances, the quantities of reagents present in each of the reagent chambers of the test cells 102 of the cartridge. The code 172 preferably takes the form of a plurality of blackened or darkened spots at selected predetermined locations through which holes 173 are formed completely through the paper cover 170. In conjunction with other predetermined locations where holes in the darkened spots are not present, light passing through the holes 173 from the transparent shelf portion 108 create a digital signal indicative of the above information pertaining to the cartridge.

Prior to inserting the flow cartridge 100 in the machine 300 (FIG. 1), a predetermined quantity of blood or other fluid is inserted into each reaction chamber 158. Typically, the blood is injected from a syringe by piercing the paper cover 170 with the syringe needle and extending the needle through the foam material 160. The injected blood collects at the bottom of the reaction chamber 158 above the upper plug member 138. After the cartridge 100 is inserted into the machine 300 (FIG. 1), the machine operatively forces the plug member 140 upward until its dome portion 148 contacts the lower edge of the partition 126. As the plug member 140 is forced upward, the slit 150 of the upper plug member 138 is forced open by pressure in the reagent chamber 152 and the reagent in the reagent chamber is forced upwardly through the passageway 128 of the partition 126 and through the open slit 150 of the upper plug member 138 and into the reaction chamber 158. The reagent 152 mixes with the blood collected in the bottom of the reaction chamber 158. Thereafter, a stream of pressurized gas is forced through the center opening 146 of the plug member 140. The pressurized gas opens the slits 150 of both plug members 138 and 140 and passes therethrough. The gas agitates the balls 156 and causes mixing of the reagent and the blood in the reagent chamber 158 and also causes bubbles of blood to be formed above the surface of the pool in the reaction chamber. The bubbles are transported upwardly by the flow of gas and contact the lower surface of the foam member 160. So long as the blood of the bubbles remains liquid, i.e., does not clot or coagulate, the liquid blood does not collect in the interstices of the foam material 160, due to the effect of the debubbling agent. When coagulation commences, the liquid blood turns to a solid or to a state of substantially higher viscosity and begins to collect in and inundate the interstices of the foam material 160, and the debubbling agent is ineffective or substantially less effective. The collection of the coagulated blood in the foam material 160 is optically sensed to detect the event of coagulation. During this operation, gas escapes out of the top of each tube-like member through the hole formed in the upper cover member 170 by the syringe needle which inserted the blood or other fluid into the reaction chamber 158.

Details of the operation of the flow cartridge are better understood by reference to the following more detailed description of the structure and operation of the machine 300.

Plunger Sensor Cartridge

Figure 5:
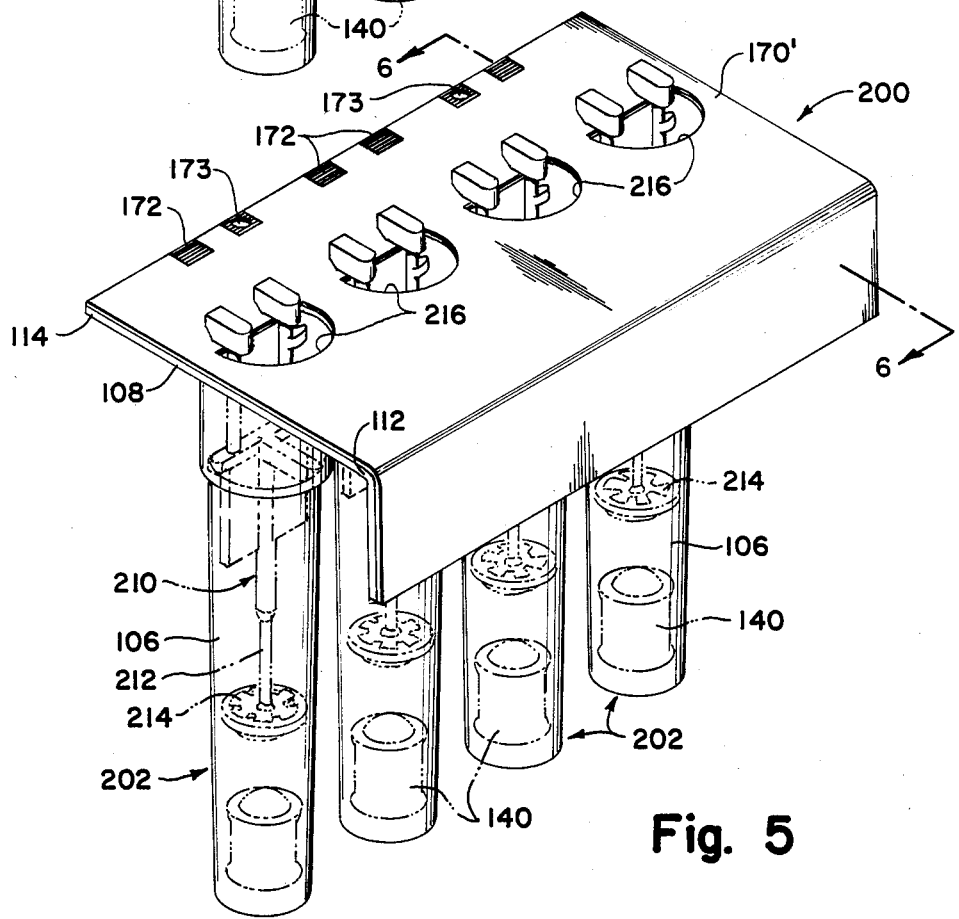
FIG. 5 is an enlarged perspective view of the plunger sensor cartridge shown in FIG. 1.
Figures 6, 7:
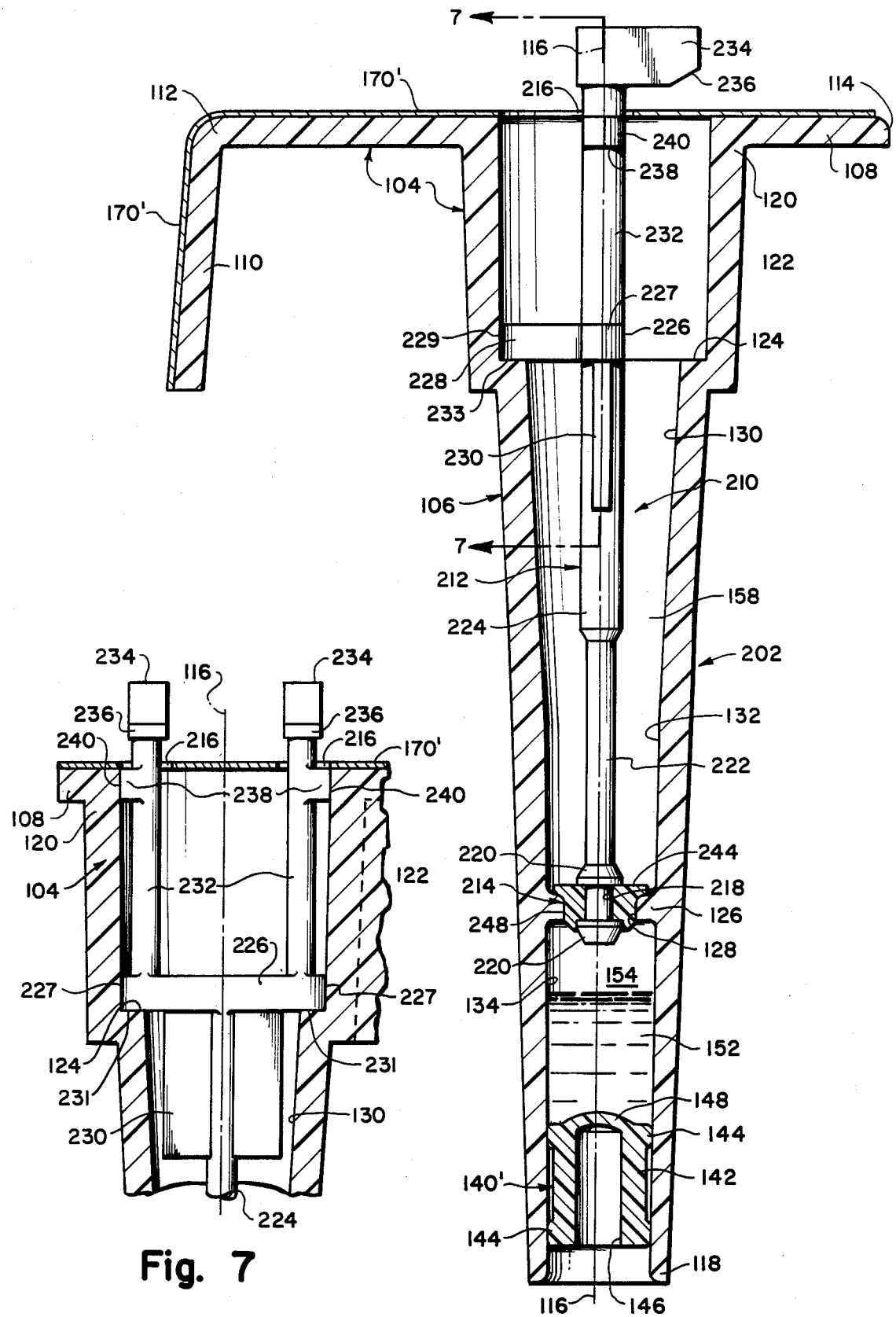
FIG. 6 is an enlarged vertical section view through one of the test cells of the plunger sensor cartridge, taken in the plane of line 6—6 shown in FIG. 5.
FIG. 7 is a partial vertical section view of the cartridge shown in FIG. 6, taken substantially in the viewing plane of line 7—7 of FIG. 6.

The plunger sensor cartridge 200 is shown in greater detail in FIGS. 5, 6 and 7. The plunger sensor cartridge 200 includes the same housing 104 employed in the gas flow cartridge 100. The elements and configuration of the housing 104 have previously been described. Each tube-like member 106 of the housing 104 defines an enclosure for each test cell 202 of the plunger sensor cartridge 200.

A plug member 140' is frictionally and slideably received within the lower interior opening of the tube member 106 defined by the surface 134. The plug member 140' is formed of the same material and has substantially the same configuration as the plug member 140 of the gas flow cartridge 100, with the exception that the dome portion 148 of the plug member 140' does not include a slit 150 (FIGS. 3 and 4). Instead, the dome portion 148 of the plug 140' is formed as a continuous integral piece of the resilient flexible material from which the plug member 140' is formed. In all other respects, however, the plug member 140' is of substantially the same configuration as the plug member of the gas flow cartridge.

A plunger assembly 210 is operatively retained within each tube-like member 106. Each plunger assembly 210 includes a plunger shaft 212 to which a disc member 214 is operatively attached at its lower end. The upper end of the plunger shaft 212 extends above a cover member 170' attached to the shelf portion 108 of the housing 104. The cover member 170' is preferably formed of paper and has the same configuration as the paper cover 170 of the gas flow cartridge 100 (FIG. 3), with the exception that holes 216 are formed through the paper cover 170' for the purpose of allowing elements of the plunger shaft 212 to move therethrough. It is apparent by comparing FIGS. 3 and 6, that the upper plug member 138, the balls 156, and the foam member 160 are utilized only in the gas flow cartridge 100, and not in the plunger sensor cartridge 200.

The disc member 214 includes a center opening 218 extending therethrough. The lower end of the plunger shaft 212 extends through the disc center opening 218. The disc member 214 is retained to the plunger shaft by and between a pair of annular flanges 220 at the lower end of the shaft 212. The disc member 214 is connected to the end of the plunger shaft 212 by expanding the resilient material of the disc member 214 and passing the lower annular flange 220 through the opening 218.

Figures 8, 9:
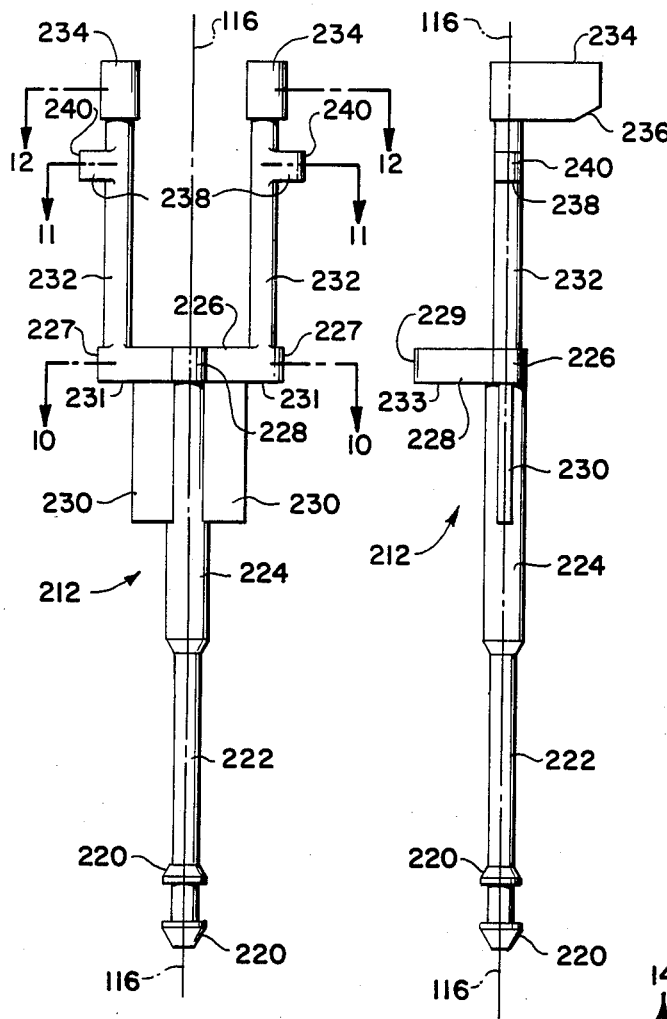
FIG. 8 is a side elevational view of a plunger shaft of a plunger assembly of the cartridge shown in FIG. 6.
FIG. 9 is another side elevational view of the plunger shaft which has been rotated ninety degrees from the view of FIG. 8.
Figure 12:
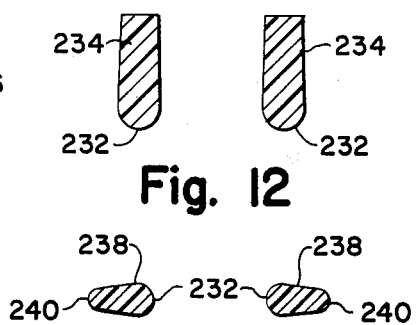
FIG. 12 is a section view taken substantially in the plane of line 12—12 of FIG. 9.
Figure 11:
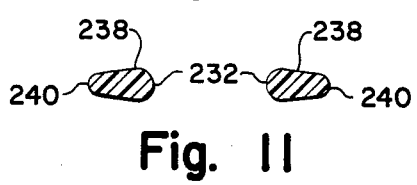
FIG. 11 is a section view taken substantially in the plane of line 11—11 of FIG. 9.
Figure 10:
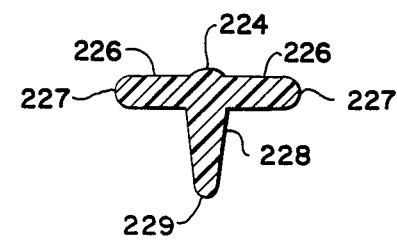
FIG. 10 is a section view taken substantially in the plane of line 10—10 of FIG. 9.

Details of the plunger shaft 212 are better illustrated in FIGS. 8 to 12. The annular flanges 220 are axially spaced at the lower end of a lower cylindrical and axially extending shaft portion 222 of the shaft 212. A slightly larger in diameter axially extending cylindrical shaft portion 224 extends upward from the lower shaft portion 222. At the upper end of the shaft portion 224, a cross member 226 extends transversely and preferably perpendicularly with respect to the axis 116 and shaft portion 224. The cross member 226 terminates at outermost opposite transverse end edges 227. As shown in FIG. 8, the cross member 226 is preferably rectangular in cross section. A projection 228 extends forwardly outward from the cross member 226 at the center location or axis 116, as shown in FIGS. 9 and 10. The projection 228 terminates at a forwardmost end edge 229. The projection 228 is also preferably rectangular in cross section, as shown in FIG. 9. A vane 230 extends below the cross member 226 and transversely outward from the upper shaft portion 224. The vane 230 extends axially approximately one half the distance downward to which the shaft portion 224 extends transversely outward slightly greater than one half the transverse distance that the cross member 226 extends from the axis 116. Lowermost surfaces 231 of the cross member 226 outward of the vane 230 and adjacent the end edge 227, and a lowermost surface 233 of the projection 228 adjacent its end edge 229, all fall coincidentally within a plane perpendicular to the axis 116 through the plunger shaft 212.

Flag shafts 232 of the plunger shaft 212 extend upward from the cross member 226 at opposite positions adjacent the outermost transverse end edges 227 of the cross member 226. In the normal position shown in FIG. 9, both flag shafts 232 extend axially parallel to the axis 116. Both flag shafts 232 are preferably cylindrical in cross section. A flag member 234 extends from the upper terminal end of each flag shaft 232. Each flag member 234 extends predominantly rearwardly from the flag shaft 232 and the axis 116, as shown in FIGS. 6 and 8. Each flag member 234 has a predominantly rectangular side configuration (FIGS. 6 and 8) with a forwardly and downwardly bevelled edge 236 at its lower rear corner. A tab 238 extends transversely outward from each flag shaft 232 at an axial position near the flag member 234 and between the flag member 234 and the cross member 226. The tabs 238 terminate at outer terminal ends 240. In the normal position of the plunger shaft shown in FIG. 9, the ends 240 of the tabs 238 project transversely outward from the axis 116 a greater distance than the distance which the outer transverse ends 227 of the cross member 226 extend. The plunger shaft 212 and its elements are preferably molded as a single integral piece relatively rigid material, such as plastic, for example polycarbonate.

Figure 13:
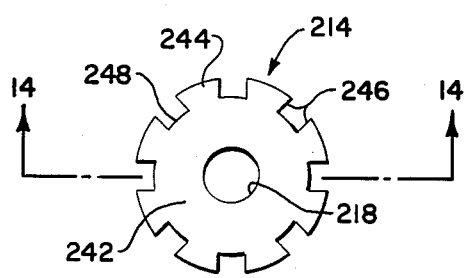
FIG. 13 is a top plan view of a plunger disc of the plunger assembly shown in FIG. 6.
Figure 14:
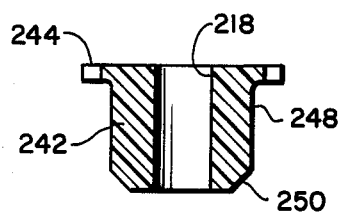
FIG. 14 is a section view taken substantially in the plane of line 14—14 of FIG. 13.

The disc member 214 of the plunger assembly 210 is shown in greater detail in FIGS. 13 and 14, and is preferably formed of a resilient flexible material such as Kraton. The disc member 214 includes a center generally cylindrical main body portion 242. An annular flange 244 extends outwardly from the main body portion 242 at its upper end. Slots 246 or generally rectangular openings 246 are formed axially through the flange 244 at equal circumferential locations. The slots 244 extend radially inward to an outer cylindrical surface 248 of the main body 242. A downwardly and axially inwardly converging bevelled edge 250 extends from the cylindrical surface 248 to the lower axial end of the main body 242. The center hole 218 extends axially through the main body 242.

One plunger assembly 210 is inserted from the upper end 120 into the interior of each tube-like member 106 of the plunger sensor cartridge 200. The plunger assembly 210 is moved downward until the outer cylindrical surface 248 of the disc member 214 is resiliently and sealingly engaged within the annular passageway 128 in the partition 126 and the flange 244 contacts the top surface of the partition 126, as shown in FIG. 6. In this operative position, the passageway 128 is sealed, as is the upper end of the reagent chamber 154 and the lower end of the reaction chamber 158. The lowermost surfaces 231 and 233 at the outer ends of the cross member 226 and the projection 228 respectively, rest on the annular shoulder 124 of the tube-like member, as shown in FIG. 7. The outer end surfaces 227 of the cross member 226 are closely adjacent to the cylindrical surface 122 of the tube-like member 106 and provide transverse stability (as shown in FIG. 7) for the plunger assembly. Stability to prevent forward tipping of the plunger assembly is provided by the projection 228, because its forward end edge 229 is closely adjacent to or contacting the cylindrical surface 122. To provide retention force for the plunger assembly 210 within the tube-like member 106, the flag shafts 232 are resiliently deflected slightly transversely inwardly toward the axis 116 at the top ends adjoining the flag members 234, as illustrated in FIG. 7, and the outer ends 240 of the tabs 238 are placed in frictional contact with the surface 122. The amount of resilient deflection of each flag shaft 232 determines the amount of retention force applied to the plunger assembly. Of course, the amount of deflection is established by the distance which the ends 240 of the tabs 238 extend outward from the flag shafts 232 past the surface 122 in the normal position of the plunger shaft 212. The plunger assembly is thereby held in the lowermost sealed position shown in FIG. 6.

The paper cover 170' can be glued to the housing 104 either before or after the plunger assembly 210 has been inserted in the manner described. The holes 216 in the paper cover 170' are sufficiently large to allow the plunger assembly 210 to be inserted into the interior or to be placed over the flag members 234.

Before the plunger assembly 210 is inserted in each tube-like member 106, the reagent chamber 154 is filled with reagent. First, the plug member 140' is inserted through the opening defined by the surface 134 at the lower end 118 of each tube-like member 106. The initial location of the plug member 140' is axially spaced between the partition 126 and the lower end 118, as shown in FIG. 6. Thereafter, the liquid reagent is added to the reagent chamber, preferably by pipetting the liquid reagent through the passageway 128 in the partition 126. Thereafter, the plunger assembly 210 is inserted into each tube-like member 106. Any increase in pressure in the reagent chamber occurring as a result of the insertion of the disc member 214 into the passageway 128 is minimal.

To utilize the plunger sensor cartridge 200, a predetermined quantity of blood or other fluid is inserted into each reaction chamber 158. Again, the predetermined quantity of blood will preferably be injected from a syringe through the hole 216. The injected blood will collect at the bottom of the reaction chamber 158 above the disc member 214. The initial lifting movement of the plunger assembly 210 withdraws the disc member 214 from the passageway 128 in the partition 126, and simultaneously the plug 140' begins moving upward until its upper surface at the dome portion 148 contacts the lower surface of the partition 126. As a result, the reagent 152 is forced into and mixes with the blood collected at the bottom of the reaction chamber 158. The initial upward movement of the plunger assembly 210 is sufficient to move the end edges 240 of the tabs 238 out of contact with the cylindrical surface 122. Once the tab end surfaces 240 are out of contact with the housing surface 122, the flag shafts 232 deflect slightly transversely outward with respect to the axis 116 and the lowermost surface of the tabs 238 extend over the top surface of the shelf portion 108. In this position, there is no frictional rubbing contact of the surfaces of the plunger assembly 210 with the housing. Thereafter, the plunger assembly 210 is repeatedly raised and released to descend downwardly through the pool of fluid collected at the bottom of the reagent chamber 158. Resistance to the vertical descent of the plunger assembly is provided by viscosity of the pool and the portions of the annular flange 244 of the disc member 214 between the openings 246 moving through the pool. The descent time of the plunger is determined by optically sensing the position of the cross member 226 and vane 230 at a predetermined time, as the plunger 210 descends. The maximum height to which the plunger 210 is lifted is not sufficient to cause the cross member 226 or projection 228 to contact the paper cover 170′. As soon as coagulation commences in the pool of fluid collected at the bottom of the reaction chamber 158, the viscosity of the liquid increases and causes a slower or retarded descent time of the plunger assembly 210. Upon sensing a predetermined increase in descent time, the event of coagulation is detected.

Details of the operation of the plunger sensor cartridge are better understood when described in relation to the specific structure and operation of the machine 300.

The Machine

Figure 15:
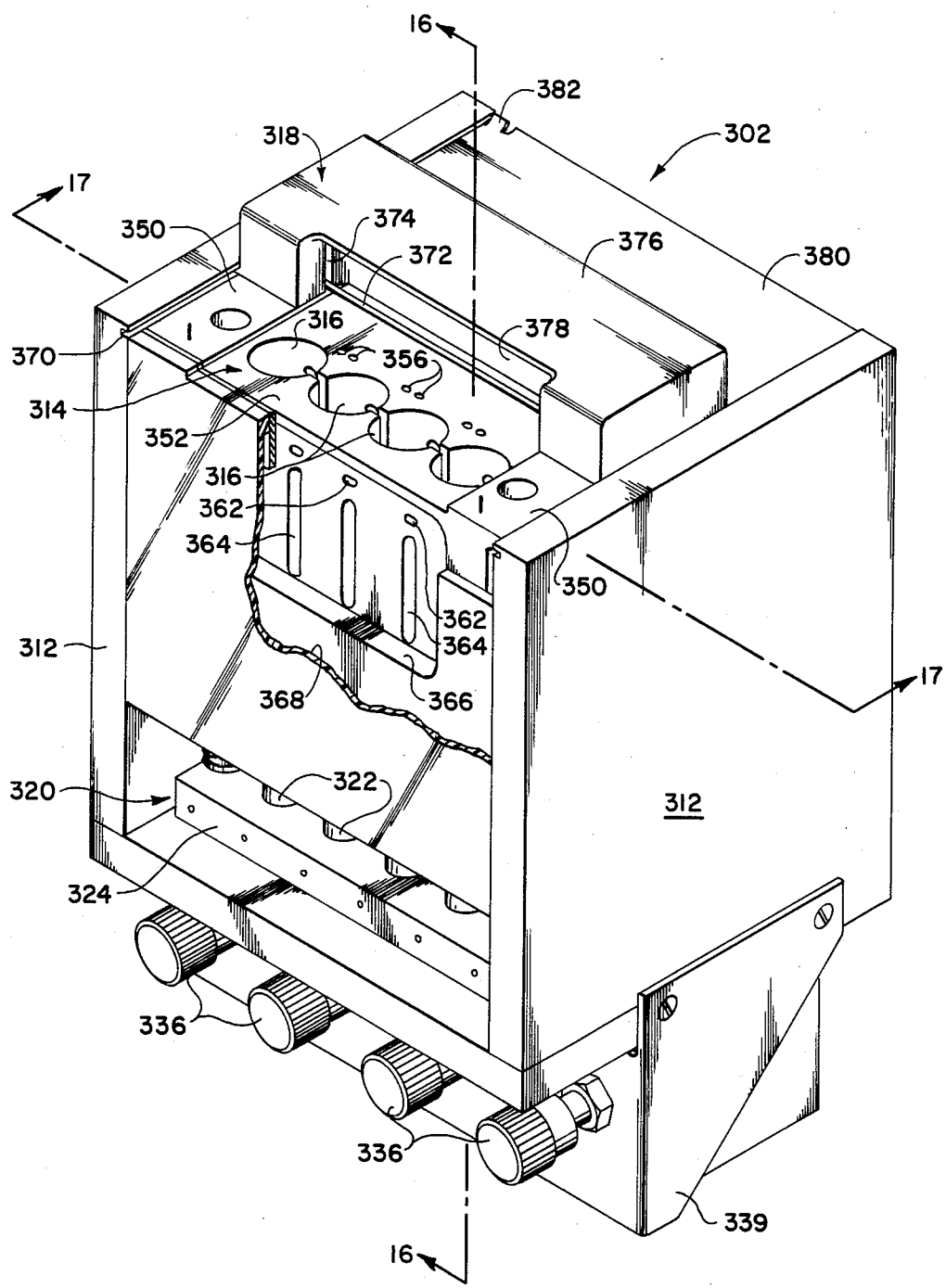
FIG. 15 is a perspective view of an actuator mechanism of the machine shown in FIG. 1.
Figure 21:
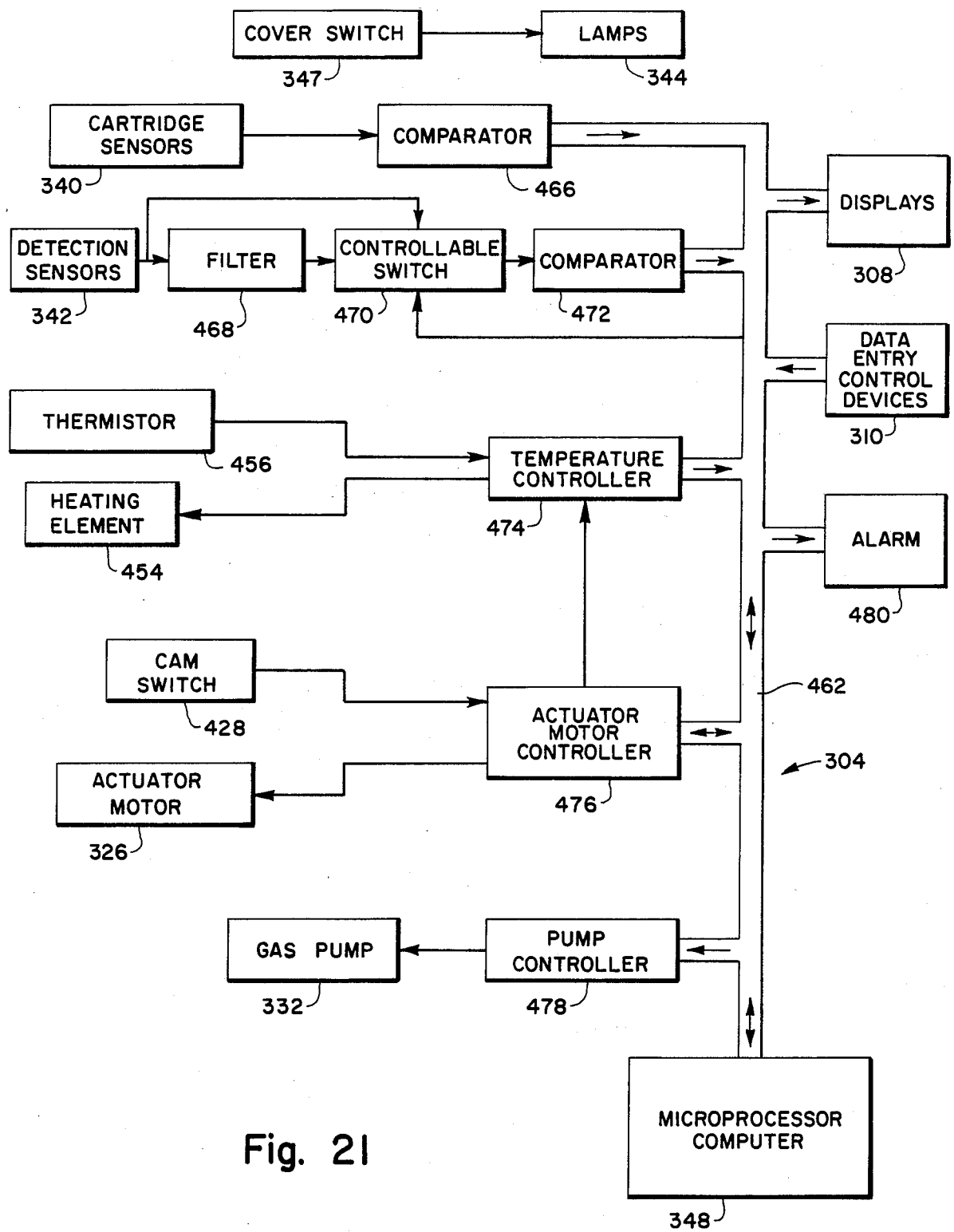
FIG. 21 is a block diagram of an operational system of the machine shown in FIG. 1.

The machine 300 is shown generally in FIG. 1, and it comprises an actuator mechanism 302 shown in FIG. 15, an operating system 304 shown in FIG. 21, and a case 306 (FIG. 1) within which the actuator mechanism 302 and the operating system 304 are substantially enclosed. Present on the exterior front of the case 306 are displays 308 for displaying information pertaining to the analytical test results and the patient. Also present are various data entry and control devices 310 for entering information into the operating system 304 and for controlling the operation of the machine 300. The case 306 is formed by a number of separate components, not specifically shown. The assembly of the components of the case 306 allows the actuator mechanism 302 and the operating system 304 to be inserted into the machine 300 during assembly.

Figure 16:
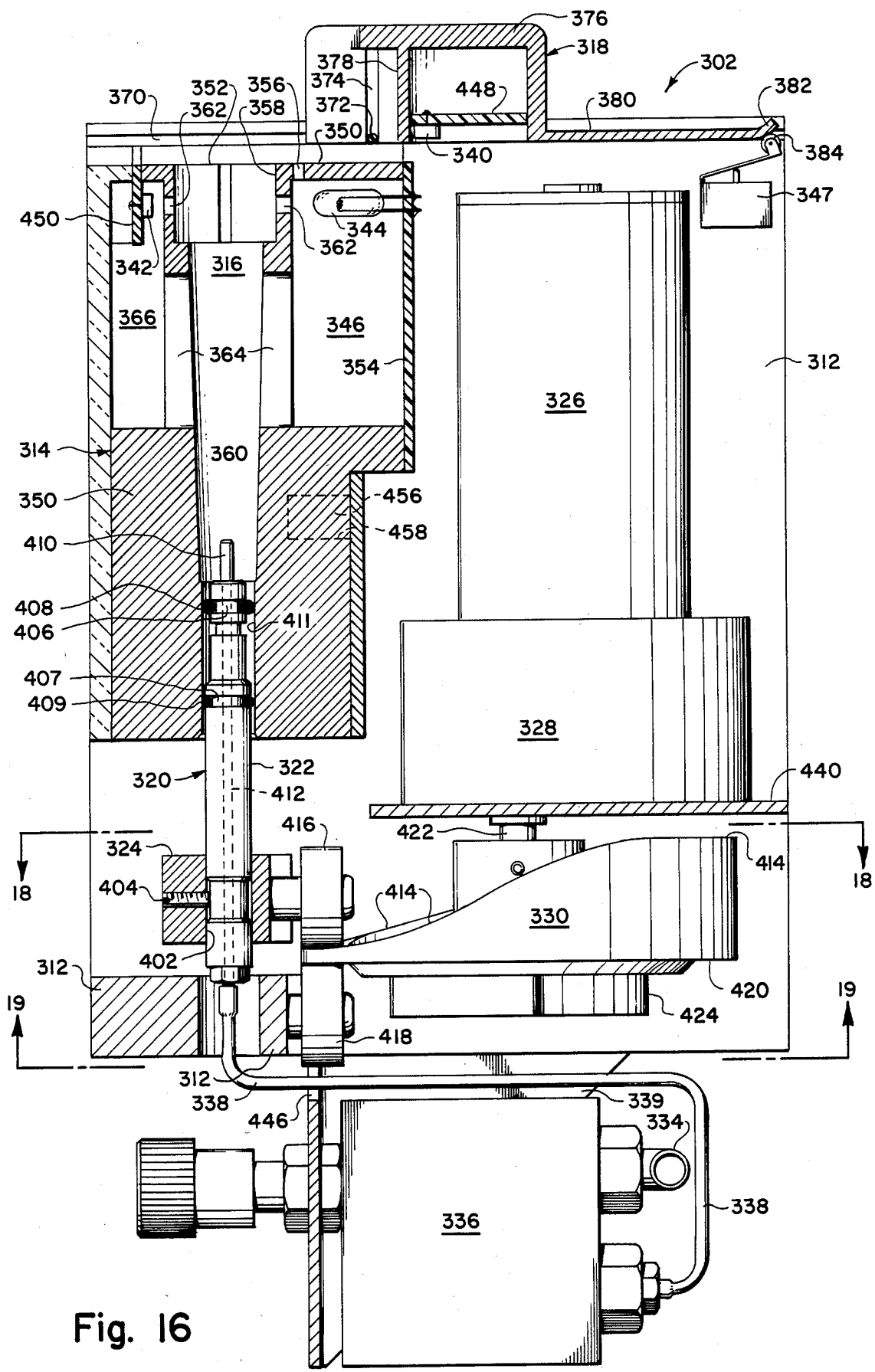
FIG. 16 is a side section view of the actuator mechanism taken substantially in the plane of line 16—16 of FIG. 15.
Figure 17:
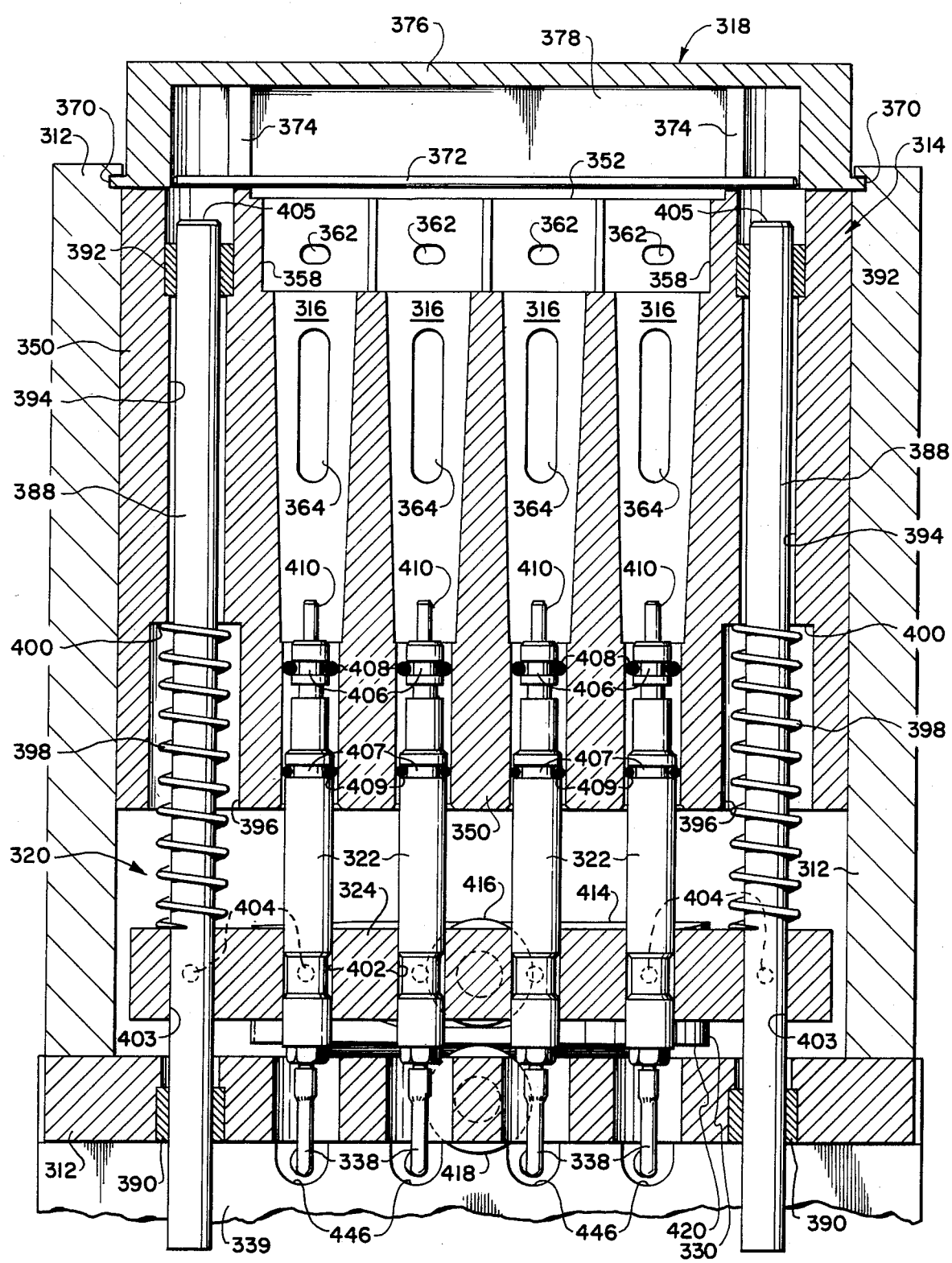
FIG. 17 is a partial front section view of the actuator mechanism shown in FIG. 15 taken substantially in the plane of line 17—17, with a top cover assembly thereof moved to a forward position with respect to the position shown in FIG. 16.

The actuator mechanism 302 is shown in FIGS. 15, 16 and 17 to comprise a frame structure, generally referenced 312, formed of a multiplicity of connected-together parts. The frame 312 retains the other components of the actuator mechanism 302 in the assembled relationship as shown.

A heat block assembly 314 is connected to the frame 312 at a position near the top and front of the actuator mechanism 302. The heat block assembly 314 includes four generally parallel and transversely spaced receptacles 316 which receive the tube-like members 106 of the flow cartridge 100 or the plunger sensor cartridge 200 (FIG. 1). A top cover assembly 318 is slidably connected to the frame 312. The top cover assembly 318 is movable between a rearward position illustrated in FIGS. 1 and 16 to expose the receptacles 316 for insertion of one of the cartridges 100 or 200, and a forward position to hold the cartridge in the actuator mechanism 302 during the analytical test, as shown in FIGS. 23A to 23E and FIGS. 24A to 24D.

Figure 23C:
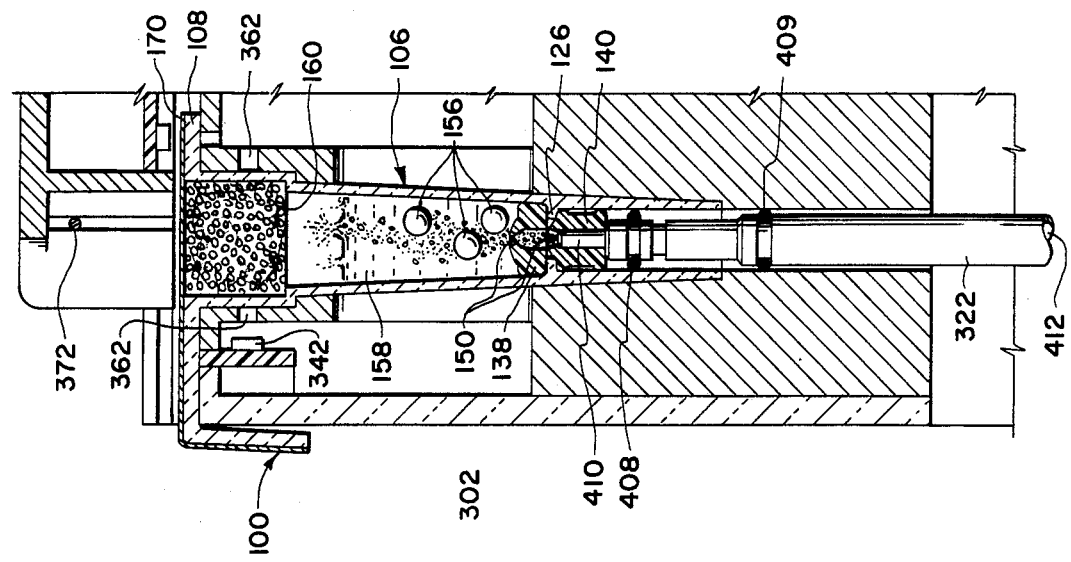
FIGS. 23A, 23B, 23C, 23D and 23E are sequential views of the gas flow cartridge shown in FIG. 2 in the actuator mechanism shown in FIG. 15, illustrating use in a coagulation detection analytical test.

A slide assembly, generally referenced 320, is retained for vertical reciprocative movement by the frame 312 and the heat block assembly 314. The slide assembly 320 includes a plurality of nozzle members 322 which are attached to and carried by a carrier block 324. One nozzle member 322 extends into each receptacle 316. Vertical movement of the carrier block 324 reciprocates the nozzle members 322 vertically in the receptacles 316. When a cartridge 100 or 200 is inserted and the slide assembly 320 is moved upward, the top of the nozzle members 322 project upwardly into the lower open ends of the tube-like members 106 (FIGS. 23A to 23E and 24A to 24D). To use the flow cartridge 100, a flow of gas is delivered through the nozzle members 322 (FIGS. 23C and 23D). To use the plunger sensor cartridge 200, the vertical reciprocating movement of the slide assembly 320 operatively lifts and drops the plunger assembly 210 (FIGS. 24A to 24D).

Means for vertically reciprocating the slide assembly 320 comprises, as is shown in FIG. 16, an electric motor 326, a reduction gear box 328 which is connected to the motor 326, and a rotational cam wheel member 330 which is rotated by the gear box 328. Rotation of the cam wheel 330 lifts and lowers the slide assembly 320.

A conventional gas pump 332 (FIG. 21) supplies pressurized gas to a manifold 334 of the actuator mechanism 302, as shown in FIG. 16. An adjustable flow control valve 336 controls the amount and the pressure of the gas flowing into each nozzle member 322. A flexible hose 338 conducts the gas from each valve 336 to its nozzle member 322. Each flow control valve 336 is connected to a bracket 339 (FIG. 15), and the bracket 339 is connected to the frame 312.

The mode of operation of the actuator mechanism 302 is determined in accordance with the type of cartridge, gas flow or plunger sensor, which is inserted into the actuator mechanism 302. The type of cartridge is optically determined by photo-optical sensors 340 carried by the top cover assembly 314, as shown in FIG. 16. Other photo-optical sensors 342 of the heat block assembly 314 optically detect the event representative of coagulation in both cartridges. The sensors 340 and 342 respond to light supplied from a lamp 344 in a light plenum 346 of the heat block assembly 314. A cover switch 347 is activated when the top cover assembly 318 is moved to the forward position, and thereafter the operating system causes the actuator mechanism 302 to function.

The operating system 304 shown in FIG. 21 controls the operation of the actuator mechanism 302. After a determination of the type of cartridge is made, a microprocessor computer 348 of the operating system 304 controls the type and sequence of operation to conduct one selected type of analytical test with the type of cartridge used. Operation of the actuator mechanism in conjunction with the gas flow cartridge 100 and plunger sensor cartridge 200 is illustrated in FIGS. 23A to 23E and 24A to 24D, respectively.

Details of the heat block assembly 314 are better understood by reference to FIGS. 15, 16 and 17. The main component of the heat block assembly 314 is a main block member 350. The block member 350 is preferably a single integral piece of aluminum or other material having good heat conducting capability and machining characteristics. Each of the receptacles 316 is preferably machined into the main block member 350. The configuration of each of the receptacles 316 is similar to and somewhat larger than the outside configuration of the tube-like members 106 (FIGS. 3 and 6) of the cartridges 100 and 200, below the upper shelf portion 108 thereof. When inserted into the receptacles 316, the upper shelf portion 108 of the cartridges 100 and 200 rests on a top surface 352 of the main block member as shown in FIGS. 23A and 24A, respectively.

The light plenum 346 is machined in the main block member 350 from a rear vertical surface thereof, as shown in FIG. 16. The lamp 344 is attached to a circuit board 354 which covers the rear opening of the light plenum 346 in the block member 350. Light from the lamp 344 is thereby confined within the plenum 346.

A plurality of cartridge detection passageways 356 extend from the plenum 346 vertically upward to the top surface 352 at positions slightly to the rear of the upper opening of the receptacles 316, as shown in FIGS. 15 and 16. When the flow cartridge 100 or plunger sensor cartridge 200 is inserted into the receptacles 316 (FIGS. 23A or 24A), the rear edge 114 of the upper shelf portion 108 extends over the detection passageways 356. The code 172 (FIGS. 2 and 5), which includes the darkened spots on the cover 170 or 170', and holes 173 through some of the spots, blocks or reduces the intensity of light passed through certain ones of the detection passageways 356 to the cartridge sensors 340 and allows light to be passed through the holes 173 to certain other sensors 340, when the top cover assembly 318 is moved to the forward position in which to vertically align the sensors 340 with the cartridge passageways 356 (FIGS. 23A and 24A). The combination of electrical signals derived from all the sensors 340 indicates the type of cartridge and information about the cartridge which is inserted into the machine. Of course, the flow and plunger sensor cartridges have different arrangements of holes 173 in the code 172 on the cover members 170 and 170' to uniquely indicate the type of cartridge and to identify the type of analytical test to be conducted with the particular type of cartridge. The signals derived by the cartridge detection sensors 310 from the code are supplied to the computer 348 of the operating system 304 (FIG. 21).

A light-conducting coagulation detecting passageway 362 and a light-conducting observation slot 364 are formed horizontally forward through each receptacle 316 from the rear light plenum 346 to a forwardly positioned light chamber 366, as shown in FIGS. 15 to 17. The coagulation detecting passageway 362 extends through an upper cylindrical surface 358 of each receptacle 316. Light within the passageways 362 penetrates and passes through the upper cylindrical surface 122 of the inserted cartridges 100 and 200 (FIGS. 23A and 24A). The observation slot 364 extends through a middle frustoconical surface 360 of the receptacles 316. The observation slot 364 exposes substantially the whole of the reaction chamber 158, between the partition 126 and the annular shoulder 124 of both the cartridges 100 and 200, to the passage of light therethrough (FIGS. 23A and 24A). A smoked Plexiglass cover 368 is attached to the main block member 350 and covers the light chamber 366. The cover 368 transmits light therethrough and is exposed at the outer surface of the machine 300 (FIG. 1). The operator can thereby visually observe the activity within the reaction chambers of the cartridges.

As is shown in FIG. 16, one coagulation detection sensor 342 is positioned in the light chamber 366 in front of each coagulation detection passageway 362. Each detection sensor 342 is electrically connected to the operating system 304 (FIG. 21) and the signals derived by the detection sensors 342 are conducted to the computer 348 of the operating system. In the flow cartridge 100, coagulation detection is achieved by a decrease in the intensity of light passed through the coagulation detection passageway 362 because the fluid coagulates in the foam member 160, as will be described more completely in conjunction with FIGS. 23a to 23E. In the plunger sensor cartridge 200, detection is achieved by the manner in which the light passed through the passageway 362 is broken by the upward and downward movement of the cross member 226 and vane 230 of the plunger assembly 210, as will be described more completely in conjunction with FIGS. 24A to 24D.

The top cover assembly 318 slides in two grooves 370 on opposite transverse sides of the actuator frame 312, as shown in FIGS. 15, 16 and 17. The components of the top cover assembly 314 are arranged to extend no lower than the plane defined by the lower surface of the slots 370. The plane of the lowermost elements of the cover assembly and the lower surface of the grooves 370 are slightly spaced above the top surface of the cover 170 or 170' on the upper shelf portion 108 of a cartridge 100 or 200 inserted into the actuator mechanism (FIGS. 23A and 24A). The cartridge sensors 340 thereby respond only to the light transmitted through each passageway 356. A lift wire 372 is carried within vertically extending slots 374 formed on opposite sides of a raised center finger grip portion 376. As is shown in FIGS. 15 and 16, the center front portion of the finger grip portion 376 is recessed at 378 rearwardly of the lift wire 372, and the lift wire 372 extends across the recess 378 without contact by other elements in the recess 378. A plate portion 380 extends rearwardly from the finger grip portion 376, as shown in FIGS. 15 and 16. The plate portion 380 is generally flat except at one rearward edge in the area adjoining one of the grooves 370, where an upturned tab 382 is formed. The tab 382 contacts an actuating member 384 of the cover switch 347 and forces the actuating member 384 to move along the underside of the plate portion 380 when the top cover assembly 314 occupies the rearward position shown in FIG. 16. When the top cover assembly 318 is moved forward, by gripping the projection 376 and pulling it forward, the actuating member 384 moves along the underside of the plate portion and up the inclined tab 382. The switch 347 is switched on and off, depending upon the upward movement of the actuating member 384. The switch 347 and its operative interaction with the top cover assembly 318 define means for signaling the establishment of conditions indicative of commencement actuator operation when the top cover assembly 318 is moved to the forward position, and for signalling the establishment of conditions indicative of termination of actuator operation when the top cover assembly 318 is moved to the rearward position.

When the top cover assembly 318 is moved forward over a flow cartridge 100 which has been inserted in the actuator mechanism, the lift wire 372 slides over the top of the paper cover 170 attached to the upper shelf portion 108 (FIG. 23A). When a plunger sensor cartridge is inserted, the forward movement of the top cover assembly 318 forces the lift wire 372 beneath the flag members 234 of the plunger assembly 210 (FIG. 24A). The beveled edges 236 are provided to direct the lift wire 372 under the flag members 234 if the lift wire should bounce upward slightly during forward movement of the top cover assembly. In this manner, the forward movement of the top cover assembly 318 readies the actuator 302 for commencement of the analytical test by positioning the lift wire 372 to lift the plunger assembly 210 from its initial position wherein the disc member 214 is inserted within and acts as a stopper for the passageway 128 in the partition 126.

The slide assembly 320 comprises a pair of transversely spaced and vertically extending slide rods 388, as shown in FIG. 17. The lower portions of the slide rods 388 are connected by bushings 390 to the actuator frame 312. Bushings 392 connect the upper portions of the slide rods 388 to the main block member 350 of the heat block assembly 314. The bushings 390 and 392 allow the slide rods to move axially therethrough. An upper opening 394 and a wider lower opening 396 extend vertically through the block member 350 to receive each of the slide rods 388. The carrier block 324 is connected to and extends transversely between the two slide rods 388. A compression spring 398 extends between the upper surface of the carrier block 324 and a shoulder 400 formed between the openings 394 and 396. The compression springs 398 bias the slide assembly 320 toward a downward position. Four openings 402 are formed through the carrier block 324 at positions axially aligned with the receptacles 316. Each opening 402 receives one nozzle member 322. Two openings 403 are formed through the carrier block 324 at positions axially aligned with the bushings 390 and 392 and the openings 394 and 396. Each opening 403 receives one slide rod 388. Set screws 404 retain the nozzle members 322 and the slide rods 388 firmly to the carrier block 324. The connections to carrier block 324 cause the nozzle members and the slide rods 388 to move vertically in unison.

The upward and downward movement of the slide rods 388 also lifts and lowers the lift wire 372. As shown in FIG. 17, upper ends 405 of the slide rods 388 align with the outer ends of the lift wire 372 when the top cover assembly 318 is in the forward position. As the slide rods move vertically, the ends 405 contact and raise and then lower the lift wire. The plunger assembly 210 is thereby lifted and lowered by the slide assembly (FIGS. 24A and 24D). The upward movement of the lift wire 372 does not influence or contact the gas flow cartridge 100 (FIGS. 23B to 23E).

The upper portion of each nozzle member 322 includes a pair of axially spaced annular recesses 406 and 407, which respectively receive O-ring seals 408 and 409, as is shown in FIGS. 16 and 17. The lower O-ring seals 409 operatively seal the nozzle members 322 against a lower cylindrical surface 411 of each receptacle 316. The upper O-ring seals 408 operatively seal the nozzle member 322 to the inside lower surface 134 of each cartridge 100 or 200 (FIGS. 23B and 24B) to prevent or retard the flow of liquids which may spill from or leak out of the cartridges 100 or 200 after analytical tests. In the gas flow cartridge 100, the upper O-ring seal 408 also assists in confirming the flow of gas through the slit 150 in the lower plug member 140.

The uppermost end of each nozzle member 322 is formed as a cylindrical projection 410, as shown in FIGS. 16 and 17. The outside diameter of the cylindrical projection 410 fits within the center opening 146 of the plug members 140 or 140' of the cartridges 100 and 200 (FIGS. 23B and 24A), when the slide assembly 320 is moved to the upper positions.

A center passageway 412 is formed through each nozzle member 322 from the upper end of the projection 410 to the lower end of each nozzle member, as is shown in FIG. 16. A supply of gas delivered from the gas pump 322 (FIG. 21) through the hose 338 flows upwardly through the passageway 412 and into the gas flow cartridge (FIGS. 23C and 23D).

Figure 18:
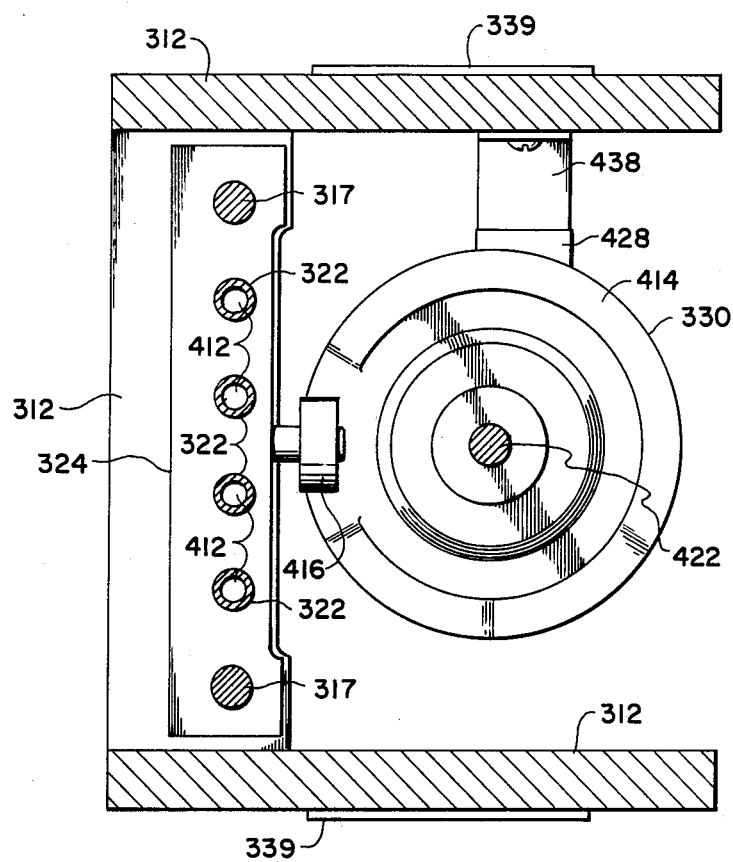
FIG. 18 is a horizontal section view of the actuator mechanism taken substantially in the plane of line 18—18 in FIG. 16.
Figure 19:
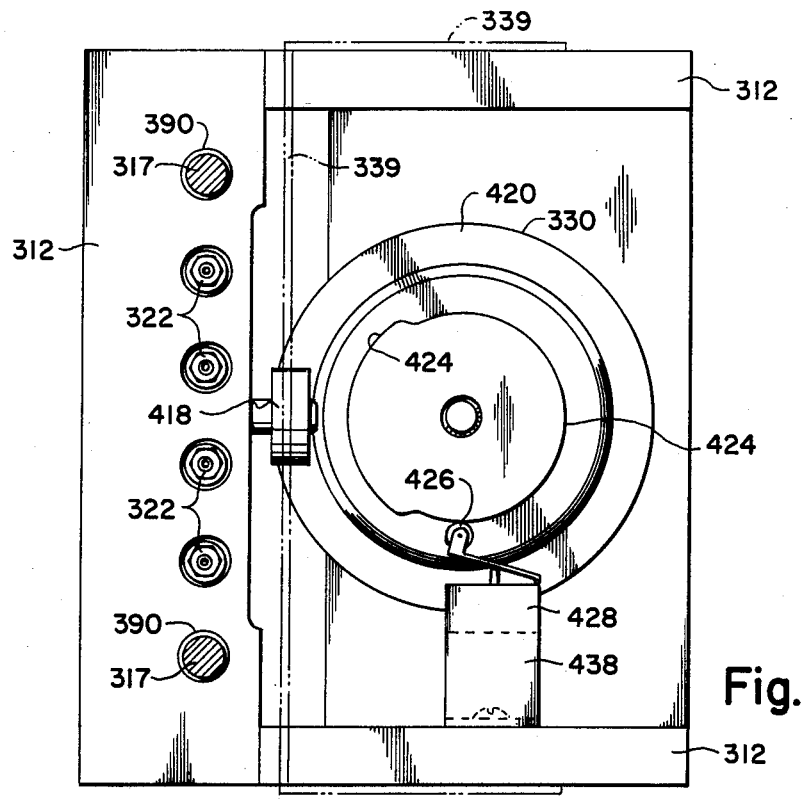
FIG. 19 is a horizontal section view of the actuator mechanism, taken substantially in the plane of line 19—19 in FIG. 16.

Rotation of the cam wheel 330 vertically reciprocates the slide assembly 320. The cam wheel 330 includes a slide assembly reciprocating axial cam surface 414 having the configuration illustrated in FIG. 20A. A cam follower roller 416 is rotationally connected to the carrier block 324, as is shown in FIGS. 16 and 18. The cam follower roller 416 rolls on and contacts the axial cam surface 414 as the cam wheel rotates. A lower stabilizing roller 418 is rotationally connected to the actuator housing 312, as shown in FIGS. 16 and 19. The lower stabilizing roller 418 contacts and rolls along a lower axial surface 420 of the cam wheel 330, and the surface 420 is perpendicular to the axis of rotation of the cam wheel 330. The stabilizing roller 418 prevents the application of any detrimental pivotal forces on the output shaft 422 of the gear box 328 when the slide assembly 320 is lifted against the bias of the spring 398, and increased lifetime is achieved.

The cam wheel 330 also includes a switching radial cam surface 424, shown in FIGS. 16 and 19. The radial cam surface 424 is contacted by an actuating roller 426 of a microswitch 428. The microswitch 428 delivers signals which control the energization of the motor 326 (FIG. 21). Hence the rotational position of the cam wheel 330 is controlled. The radial contour of the cam surface 424 is illustrated in FIG. 20B. By comparing FIGS. 20A and 20B, which are illustrated on a common horizontal axes referenced to similar operational rotational positions of the cam wheel 330, it can be seen that the switch points 430 and 432 of the microswitch 428 occur at the rotational positions of the cam wheel which provide maximum axial displacement 434 and minimal axial displacement 436, respectively. Accordingly, the microswitch 428 supplies a signal each time the motor 326 rotates the cam wheel 330 into a position in which the maximum upward and minimum downward vertical movement of the slide assembly 320 is achieved. As shown in FIGS. 20A and 20B, cam surface 314 maintains the maximum axial displacement 434 and minimum axial displacement 436 over a predetermined rotational angle, so the rotational inertia of the cam wheel, gear box and motor will not rotate the cam wheel past the maximum and minimum positions after the motor is de-energized. The microswitch 428 is attached to the actuator housing 312 by a conventional fastener 438, shown in FIG. 18.

As is shown best in FIG. 16, the motor 326 is attached to the gear box 328, and the gear box 328 is connected to a support plate 440. The support plate 440 is attached to the actuator frame 312 by conventional means (not shown). The output shaft 422 of the gear box 328 extends through the plate 440 and connects to the cam wheel 330. Openings 446 are provided in the gas flow valve attachment bracket 339 to allow the flexible hoses 338 to extend from the output flow ports of the flow valves 336 to the input flow ports of the nozzle members 322. The hoses 338 are of sufficient length and flexibility to move upward with the slide assembly without disconnecting from the output ports of the flow control valves 336 or the input ports of the nozzle members 322.

Figure 22:
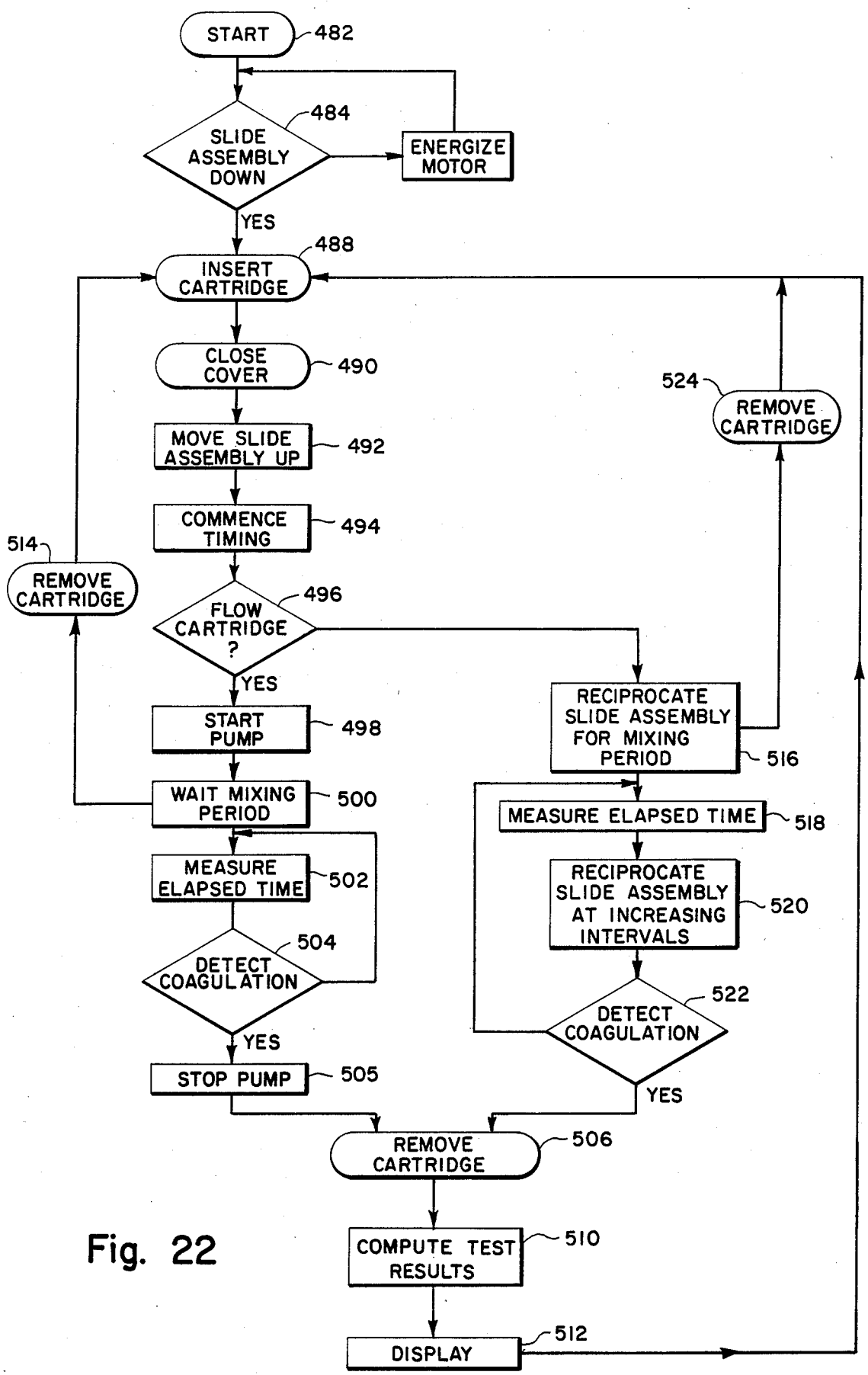
FIG. 22 is a flow diagram of the basic operational features of the system shown in FIG. 21.

Circuit boards 448 and 450 respectively mount the cartridge photosensors 340 and detection photosensors 342 to the actuator mechanism 302. The photosensors 340 and 342 are directly connected to the circuit boards 348 and 350 and the circuit boards 348 and 350 are attached by conventional fastening means to the top cover assembly 318 and the heat block assembly 314, respectively. The lamp 344 is directly attached to the circuit board 354, which is attached to the rear surface of the main block member 350. A flat heating element 454 is attached to the lower rear surface of the main heat block member 350. A temperature sensor means such as a thermistor 456 is inserted through a hole in the heating element 454 into a receptacle 458 formed forward from the lower rear surface of the main heat block member 350. The output signal from the thermistor 456 is related to the temperature of the main heat block member 350. The main heat block member 350 is heated by passing current through the electrical resistance of the heating element 454. The signal from the thermistor 456 operatively controls the energization of the heating element 454. The computer of the operating system (FIG. 21) monitors the temperature sensed by the thermistor until a predetermined operating temperature is reached. Once the operating temperature is reached, the computer 348 commences execution of the operating sequence (FIG. 22).

During blood coagulation analytical tests, it is important to maintain the temperature of the heat block member 350 and hence the fluid contained within the cartridges at a predetermined established test temperature. This predetermined test temperature has been recognized medically as a standard for blood coagulation analytical tests.

The circuit boards and the electrical components of the actuator mechanism are connected by electrical conductors (flexible where necessary or required). Components of the operating system 304 are mounted on other circuit boards, not shown, which are retained internally within the case 306 of the machine 300 (FIG. 1), and these components are likewise connected by conductors.

The details of the operating system 304 is better understood by reference to FIG. 21. The microprocessor computer 348 controls the operation of the machine 300 to accomplish the coagulation related analytical tests with the gas flow and plunger sensor cartridges. Various elements associated with the actuator mechanism 302 are operatively connected with the microprocessor computer 348 over a main signal bus 462. The displays 308 and the data entry and control devices 310 on the exterior casing of the machine 300 (FIG. 1) are also operatively connected to the microprocessor computer 348 over the signal bus 462. Digital signals are conducted over the bus 462, to and from the computer 348, in the conventional manner.

The cover switch 347 directly activates the lamps 344 within the light plenum 346 (FIG. 16). Execution of the operating sequence (FIG. 22) commences when the cartridge sensors 340 detect light, as a result of closure of the top cover assembly.

The signals from the cartridge sensors 340 are supplied to a comparator 466. The comparator 466 receives the signals from the cartridge sensors 340, compares the cartridge sensor signals to predetermined signal levels, and supplies a computer compatible signal to the signal bus 462 representing the state of the cartridge sensor signal. Upon receipt of the signals from the comparator 466, the computer 348 is able to distinguish the type of cartridge, either gas flow or plunger sensor, which has been inserted into the actuator mechanism and to determine the type of analytical test to be executed with that type of cartridge. The signals from the comparator 466 indicate when the top cover assembly is closed, and the comparator 348 is signalled to commence the operating sequence.

The coagulation detection sensors 342 supply signals to a filter 468 and to a controllable switch 470. Signals from the switch 470 are supplied to a comparator 472, and the comparator 472 supplies signals to the computer 348 over the signal bus 462. Control signals are supplied to the switch 470 by the computer over the signal bus, and these control signals control the switch 470 to conduct signals from the filter 468 to the comparator 472 or to conduct signals from the detection sensors to the comparator 472. The filter 468 is a band pass filter for filtering out spurious short-duration high-frequency signals and base line shifts. As will become more apparent in the description of FIGS. 23A to 23E, it is advantageous to employ the band pass filtering characteristics of the filter 468 to detect coagulation with the gas flow cartridge 100. However, when detecting coagulation by the plunger sensor cartridge 200, as shown in FIGS. 24A to 24D, rapid response times are required. In this case, the signals from the detection sensors 342 are directly supplied to the comparator 472. The control signal from the computer 348 to the switch 470 causes the signals supplied by the switch 470 to be in the proper form in accordance with the type of cartridge 100 or 200 in use. The comparator 472 compares the signal delivered by the switch 470 to a predetermined signal level, and supplies a signal on the bus 462 when changes are detected.

The thermistor 456 supplies a signal directly to a temperature controller 474. The temperature controller 474 directly controls the energization of the heating element 454. The signals delivered by the thermistor 456 to the temperature controller 474 cause either the energization or the de-energization of the heating element 454 in accordance with whether the actual sensed temperature is less than or greater than, respectively, the predetermined temperature established for the analytical test. The temperature of the main heat block member 350 (FIG. 16) is communicated by signals from the temperature controller 474 to the computer 348 over the bus 462. The computer 348 monitors the temperature sensed by the thermistor 456 on a periodic basis and provides a warning not to commence the test until the temperature of the main heat block member has reached its predetermined level.

Signals from the cam switch 428 are supplied to a motor controller 476, and the motor controller 476 directly controls the energization of the motor 326. The motor controller 476 is connected to the computer 348 over the system bus 462. The computer 348 signals the motor controller 476 to energize the actuator cam motor 326 and signals from the switch 428 cause the motor controller 476 to de-energize the motor 326 when the slide assembly 320 reaches a maximum upward position or a maximum downward position, as respectively represented at 434 and 436 in FIGS. 20A and 20B. Signals from the controller 476, which indicate the position of the cam wheel and hence the slide assembly, are supplied to the computer 348 over the data bus. The time duration during which the slide assembly remains in the maximum upward or maximum downward position is established by a timing function of the computer 348 or by recognition of the type of cartridge, gas flow or plunger sensor, which is in use.

Signals from the actuator motor controller 476 are also supplied to the temperature controller 474. The temperature controller 474 is disabled to prevent further energization of the heating element 454 when the motor 326 is energized, to prevent excessive current consumption and drain. The thermal retention capability of the main heat block member essentially maintains the established test temperature during times when the motor 326 operates.

The gas pump 322 is energized by a controller 478. The controller 478 is connected to the computer 348 over the system bus 462. Signals from the computer 348 are delivered to the controller 478 to cause energization of the gas pump 322.

The displays 308 and data and entry control devices 310 present on the exterior of the case 306 of the machine 300 (FIG. 1) are directly connected to the system bus 462. Signals from the microprocessor computer 348 are delivered directly to the displays 308 in a time multiplexed fashion. Signals from the data entry and control devices 310 are also directly supplied to the microprocessor computer 348. In addition, an alarm 480 may be provided. The alarm 480 may signal the user of the conclusion of an analytical test, or test results which fall outside of predetermined limits or the failure to achieve suitable test results within a predetermined time, for example.

The displays 308, data entry and control devices 310, alarm 480, comparators 466 and 472, filter 468, controllable switch 470, and controllers 474, 476 and 478, are all conventional items.

Operation

The operational sequence of the machine 300 with either the gas flow cartridge 100 or the plunger sensor cartridge 200, and the general features of the operating program of the microprocessor computer 348, are illustrated by FIG. 22. Prior to the commencement of operation as referenced at 482, the temperature of the main heat block member is allowed to reach its pre-established operating temperature. Thereafter, the computer also monitors the temperature of the main heat block member from time to time to check the predetermined established temperature. A determination of the position of the slide assembly is made at 484. If the slide assembly is up, the cam motor 326 is energized until the slide assembly has reached its maximum downward position. Under these conditions, the machine is ready to commence an analytical test.

A cartridge is inserted at 488 and the top cover assembly 318 is manually closed or moved to the forward position, as shown at 490. The computer recognizes that the top cover assembly has been closed by the signals from the cartridge detectors, which are created by energization of the lamps 344 by the switch 347 (FIG. 21). After closing the top cover assembly 318, the computer 348 delivers signals to energize the cam motor 326 and cause the slide assembly 320 to raise its maximum upper position as referenced at 492. In both the gas flow cartridge 100 and plunger sensor cartridge 200, the initial upward movement of the slide assembly pushes the plug members 140 and 140' upward against the partition 126. The contents of the reagent chamber 154 are pushed into the reaction chamber 158. The measurement of the elapsed time for the analytical test is immediately commenced at 494.

Substantially simultaneously, a determination is made at 496 of the type of cartridge inserted into the machine. If the cartridge inserted is a gas flow cartridge 100, the computer 348 immediately causes energization of the gas pump 322, at 498. The gas flowing through the gas flow cartridge 100 mixes the contents in the reaction chamber for a predetermined mixing period, which is timed and established by the computer, as referenced at 500. After the mixing period referenced at 500, the computer measures the elapsed time at 502 until coagulation is detected at 504. Until coagulation is detected, measurement of the elapsed time continues at 502. Once coagulation has been detected in all the test cells 102 or otherwise in accordance with the limitations of the test as indicated at 504, operation of the gas pump 322 is terminated at 505. The cartridge is removed from the machine at 506. The data from the test is computed at 510 and displayed on the front of the machine 300 at 512. The results and data will continue to be presented at 512 until a new cartridge is thereafter inserted at 488 or new data concerning the patient is entered by the devices 310.

Should the analytical test with the gas flow cartridge be interrupted or the cartridge removed at 514, the program will return to the position referenced at 488 and remain in a state ready to commence operation upon the insertion of a new or different cartridge.

If the determination is made at 496 that a gas flow cartridge is not inserted into the machine, the operating procedure for a plunger sensor cartridge 200 is thereafter followed. At the start of the operating procedure for the plunger sensor cartridge, the computer 348 causes the cam motor 326 to reciprocate the slide assembly 320 to initially mix the reagent and the contents in the reaction chamber, as referenced at 516. After the slide assembly 320 has been reciprocated for the mixing period, the computer commences measuring the elapsed time for the analytical test as indicated at 518. During the analytical test, the slide assembly 320 is reciprocated by the computer 348 operatively causing the cam motor 326 to be energized. The interval between each upward and downward reciprocation of the slide assembly is increased in relation to the total elapsed time of the test. In those circumstances where coagulation occurs only after a relatively long elapsed time period, the clot formation is not adversely affected if the intervals between individual reciprocations are extended in relation to the elapsed time of the test. Until coagulation is detected at 522, the elapsed time of the test is continually measured at 518 and the slide assembly is continually reciprocated at 520. Once detection of coagulation is made at 522, the cartridge is removed at 506. The data from the test is computed at 510 and displayed at 512. The results of the test are continually displayed at 512 until a new cartridge is inserted or new patient data is entered. Upon removal of the cartridge at 508, the machine is ready to receive a new cartridge, inserted at 488.

Should the plunger sensor cartridge be removed at 524 prior to the detection of coagulation, or the test otherwise interrupted, the operating sequence will become ready to conduct a new test at 488.

Details of the use and operation of the gas flow cartridge 100 in the actuator mechanism 302 are better understood by reference to FIGS. 23A, 23B, 23C, 23D and 23E in sequence. In FIG. 23A, the gas flow cartridge 100 has been initially inserted into the machine and the top cover assembly 318 has been moved to its forward or closed position. Of course, previous to insertion of the cartridge 100 into the machine, a predetermined quantity of human blood 530 or other fluid upon which a coagulation-related test is to be conducted has been inserted into the reaction chamber 158. The upper cover 170 has been pierced when the blood 530 was inserted, usually with a syringe and its needle. Insertion of the cartridge 100 into the actuator mechanism 302 forces each center opening 146 in each plug member 140 down over each upper projection 410 of each nozzle member 322. A relatively firm friction seal and fit is established between the walls of the plug member 140 at the center opening 146 and the projection member 410.

Figure 23B:
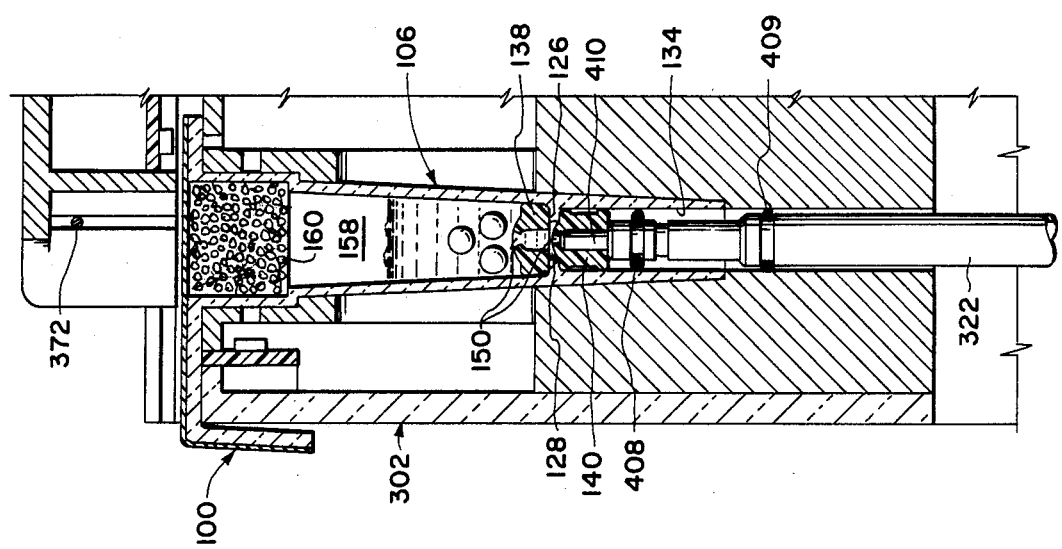
Figure 23A:
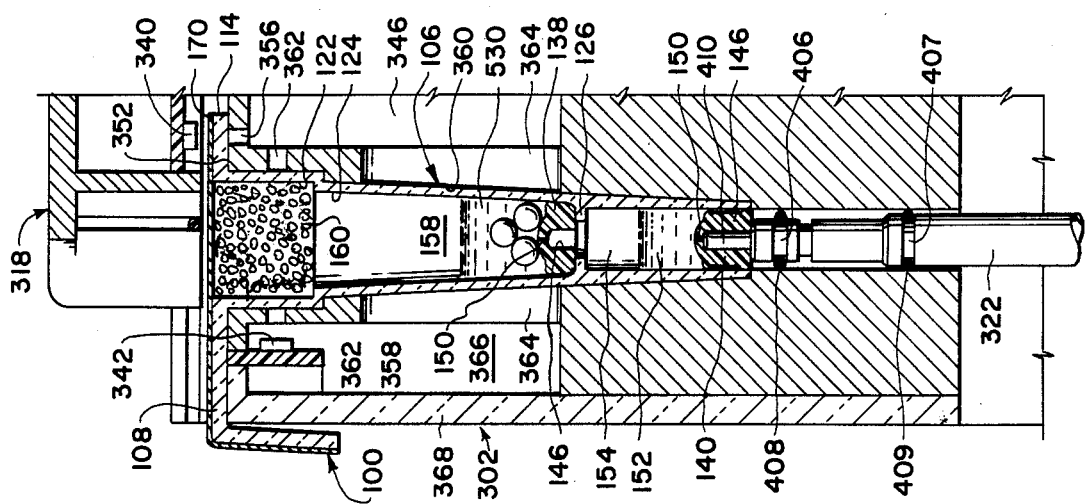
Figure 23D:
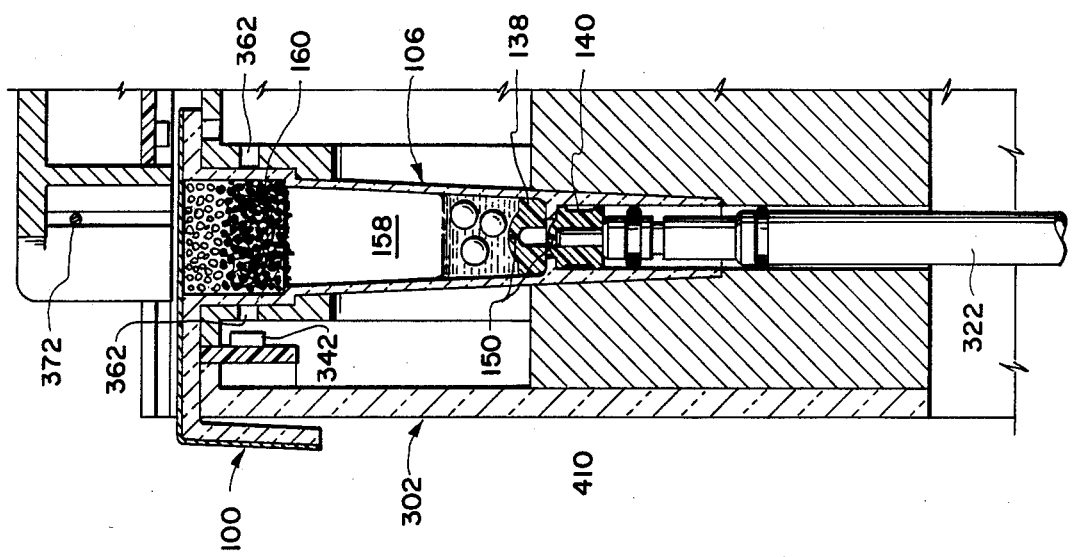

The initial upward movement of the slide assembly causes each nozzle member 322 to slide upward within and along the lower cylindrical wall surface 134 of the tube-like member 106 until the plug member 140 contacts the partition 126, as is shown in FIG. 23B. The O-ring seals 408 seal against surface 134. The slit 150 in the upper plug 138 is opened by the increased pressure in the reagent chamber 154, and the contents of the reagent chamber 154, including the reagent 152, are forced into the reaction chamber 158. During the duration of the analytical test, the slide assembly 320 and its nozzle members 322 remain in the maximum upward position illustrated in FIGS. 23B to 23E, and referenced at 492 in FIG. 22.

Gas is delivered from the gas passageway 412 (FIG. 16) in the nozzle member 322 through the separated slits 150 in the lower and upper plug member 140 and 138, respectively, into the reaction chamber 158, as shown in FIG. 23C. The O-ring seals 408 confine the gas to this upward flow path. The gas is so delivered during the mixing period referenced at 500 in FIG. 22, and during the timing of the elapsed time of the analytical test referenced at 502 in FIG. 22. The gas moves upward through the contents of the reaction chamber 158 and causes random bouncing movement of the balls 156 to further agitate, mix and activate the fluids in the reaction chamber 158. The gas moves upward through the fluid contents of the reaction chamber 158, the foam member 160, and out of the open interior at the upper end of each tube-like member 106 through the hole formed in the paper cover 170.

As is shown in FIG. 23D, the bubbles of liquid carried by the gas flowing upward through the liquid contents of the reaction chamber 158 carry with them a small amount of the liquid from the reaction chamber. The liquid of the bubbles moves no further upward into the foam member 160 than its lowermost surface. So long as the liquid is not coagulating, the debubbling agent with which the foam member 160 has been treated causes the liquid to drain down off of the foam member 160. The liquid drains down from the foam member 160 and back into the pool at the bottom of the reaction chamber 158. The intensity of light transmitted through the coagulation detection passageway 362 to the detection sensor 342 remains essentially at its previous level. The light path through the foam member 160 is uninfluenced because the level of the uncoagulated liquid never reaches the height of the light path.

Figure 23E:
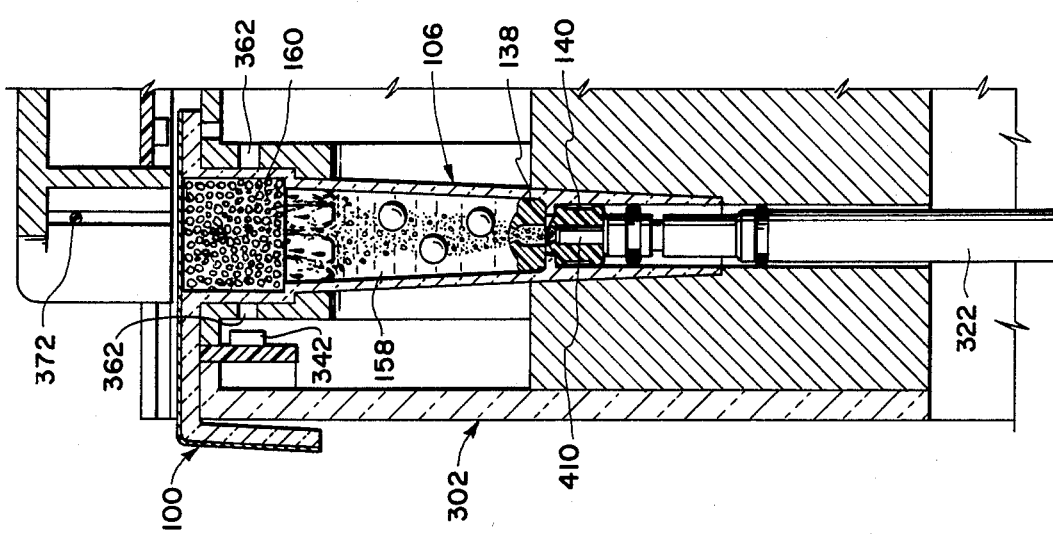

As is shown in FIG. 23E, the liquid carried by the bubbles to the top of the reaction chamber 158 penetrates upward into the foam member 170 and collects approximately throughout the lower half of the foam member 160 when coagulation occurs. The debubbling agent on the foam member becomes ineffective to repel coagulated fluid. Under these circumstances, the light passing through the foam member 160 is blocked or significantly reduced in intensity. The detection sensors 342 sense the condition in the foam member and deliver a signal indicative of coagulation. The filter 468 (FIG. 21) is operated in its band pass mode to prevent spurious momentary build-ups in the foam member from causing an early indication of coagulation before the full light path through the foam member becomes blocked.

Depending upon the analytical test, it may continue until coagulation is detected in all of the tube-like members 106 of each cartridge 100 or it may be terminated after coagulation is detected in the first one or two of the tube-like members 106. Of course, after coagulation is detected, the flow of gas through the nozzle members 322 is terminated. The slits 150 in the upper and lower plug members return to their nondistended positions when the gas flow terminates to seal the bottom of each tube-like member 106 against the flow of liquid out of the bottom of the reaction chamber 158.

Details of the operation and use of the plunger sensor cartridge 200 to detect coagulation in an analytical test are better understood by reference to FIGS. 24A, 24B, 24C and 24D, in sequence. In FIG. 24A, the top cover assembly 318 has been moved to the forward or closed position. The lift wire 372 is carried forward in the groove 374 with the top cover assembly 318 and slides under the flag members 234 of each plunger assembly 210.

The simultaneous initial upward movements of the plunger assembly 210 and the plug member 140' are illustrated in FIG. 24B. The upward movement of the lift wire against the flag members 234 lifts the plunger assembly 210 upward, thereby lifting the outer cylindrical surface 248 of the disc member 214 from its sealed relationship within the passageway 128 of the partition 126. The ends 240 of the tabs 238 (FIGS. 7 and 9) move upward through each hole 216 (FIG. 5) and above the cover 170' of the tube-like members 106. Each plunger assembly 210 is thereby freely positioned within the interior opening of each tube-like member 106 of the cartridge 200 and suspended from the lift wire 372. The plunger assembly 210 can therefore be lifted and dropped without resistance except for that encountered by the movement of the disc member 214 through the liquid within the reaction chamber 158. With the first initial upward movement of the slide assembly 320, the nozzle members 322 push the plug members 140' upward against the partition 126. The contents 152 of the reagent chamber 154 are forced into the reaction chamber 158. Because the nozzle members 322 move upward in unison with the lift wire 372 due to action of the slide assembly, the disc member 214 moves out of sealing engagement with the passageway 128 simultaneously with the upward movement of the lower plug member 140'. Pressure does not build up in the reagent chamber. Splattering of the contents of the reagent chamber into the reaction chamber is thereby avoided. Once the plug member 140' reaches its upward position against the partition 126, all the contents are present in a pool in the bottom of the reaction chamber 158.

The contents of the reaction chamber 158 are initially mixed as referenced at 516 in FIG. 22. Mixing occurs by repeatedly lifting the plunger assembly 210 as shown in FIG. 24B and dropping or releasing the plunger assembly 210 to allow the disc member 214 to descend through the pool of fluid in the reaction chamber 158, as shown in FIG. 24C. The upward lifting movement of the slide assembly 320 occurs at a slower rate than the downward movement of the slide assembly, as is illustrated by the left-hand rising portion of the cam curve 414 shown in FIG. 20A, as compared to the right-hand descending portion of the cam curve 414. The rapid descent of the slide assembly is facilitated by the rapidly descending portion of the cam curve and the downward force from the compression springs 398 (FIG. 17). The downward movement of the slide assembly 320 occurs at a sufficiently rapid rate to essentially free the plunger assembly 210 from any contact or effect from the lift wire 372, as shown in FIG. 24C. The plunger assembly 210 is therefore free to descend only under the influence of gravity and the flow resistance caused by movement through the pool of liquid in the reaction chamber 158.

After the initial upward movement of the plug member 140', the plug member 140' remains at the upward position contacting the partition 126. The upper projection 410 of the nozzle member 322 is readily withdrawn from and inserted into the center opening 146 of the plug 140' as the nozzle member 322 is vertically reciprocated. This condition is illustrated in FIG. 24C.

The descending of the plunger assembly 210 breaks or temporarily blocks the light beam passing through the detection passageway 362 and received by the detection sensor 342. When the plunger assembly 210 is in its upper positions, as is illustrated in FIGS. 24B and 24C, the vane 230 and cross member 226 break the beam of light passed through the detection passageway 362. In the lower position illustrated in FIG. 24A, the vane 230 and cross member 226 do not obstruct the light passed through the detection passageway 362. The use of the two flag shafts 232 near the transverse ends of the cross member 226 (FIG. 7) provide an open space therebetween which also does not interfere with the light passed through the detection passageways 362. A signal is supplied by each of detection sensors 342 when the plunger assembly 210 reaches the lower positions in its descent within the tube-like members 106.

After the initial mixing period, timing of the analytical test commences, as is illustrated at 518 in FIG. 22. The plunger assembly 210 is repeatedly lifted and allowed to drop or descend through the pool of fluid in the reaction chamber 158. The descent through the pool of fluid is sensed by waiting a predetermined time period after the plunger assembly is released and then checking the signals from the photosensors 342 to see if the plunger assembly 210 has fallen to a position where the light beam is no longer broken. When the plunger has not descended significantly at the predetermined time period after which the plunger assembly is released, indicated by the light beam remaining blocked at the end of the time period, an indication of detection is registered.

The interval between each complete reciprocation of the slide assembly and hence lift and descent of the plunger assembly 210, is lengthened in relation to the total elapsed time of the analytical test. For example, at earlier stages of the analytical test, the plunger assembly 210 may be raised once every two seconds and allowed to descend, but in later stages of the analytical test, the plunger assembly 210 may be raised once every twenty-five seconds and allowed to descend. It has been discovered that, in blood coagulation related analytical tests where coagulation occurs a considerable length of time after the test commences, the strands or fibers of material which coagulate are particularly delicate. If the plunger assembly was to be lifted and allowed to descend at equal relatively rapid intervals, the fibers would never achieve full coagulation because they would be constantly agitated and broken by the upward and downward movement of the plunger assembly. However, by allowing relatively longer intervals as the test progresses, the relatively delicate fibers are allowed to form and coagulation can be sensed. In those tests where coagulation occurs at a relatively shorter elapsed time, the strength of the fibers and strands formed by coagulation is sufficient to provide an indication of coagulation at the shorter intervals between each lifting and descent of the plunger assembly 210. Initially, a predetermined time period between intervals is established. Once the interval between initiating reciprocations of the slide assembly is equal to three percent to seven percent of the total elapsed time, the interval is increased to equal to three to five percent of the total elapsed time. An interval increasing at the rate of five percent of the total elapsed time is regarded as preferable in blood coagulation-related tests.

Coagulation is indicated when the plunger assembly 210 descends very slowly or not at all through the pool of coagulated fluid in the bottom of the reaction chamber 158, as shown in FIG. 24D. In situations where the plunger assembly fails to descend through the pool in the bottom of the reaction chamber, the vane 230 and cross member 226 block the light transmitted to the sensor detector 342. In situations where the plunger assembly descends relatively slowly through the pool in the bottom of the reaction chamber 158, the light beam remains blocked at the end of the predetermined time period allowed for checking the position of the plunger assembly. Once the descent time takes greater than this predetermined period, the computer 348 recognizes that coagulation has taken place. The predetermined time period for checking the descent and position of the plunger assembly may vary in relation to the type of fluid in which coagulation is being detected.

From the foregoing description, it can be appreciated that the machine 300 is capable of accepting either a gas flow cartridge 100 or a plunger sensor cartridge 200, and conducting an analytical test in accordance with either type of cartridge. The analytical tests with either type of cartridge are conducted quickly with automated repeatable exactness. The detection of coagulation is reliably perceived with both types of cartridges and accurate test results are derived. By allowing selective alternate use of the types of cartridges and the types of tests to be conducted, the best conditions can be established for conducting the dose response, clotting time and titration tests in therapeutic situations where relatively small doses of heparin or anticoagulant are administered. The gas flow cartridge usually offers superior accuracies in the dose response and clotting time tests, and the plunger sensor cartridge usually offers superior accuracies in titration tests. Furthermore, all three types of coagulation tests can be conducted on a selective basis, and accurate results are assured from each test.

The nature and operation of the present invention has been shown and described with a degree of specificity. It should be understood, however, that the specificity of the description has been made by way of preferred example and that the invention is defined by the scope of the appended claims.

What is claimed is:
1. A cartridge in which to conduct a coagulation-related analytical test on fluid, comprising:
   a tube-like member having an open interior extending generally axially therethrough from an open lower end to an upper end;
   a partition of the tube-like member located within the open interior at a position intermediate the upper and lower ends of the tube-like member, said partition generally dividing the open interior into a lower chamber between the partition and the lower end and into an upper chamber between the partition and the upper end;

a passageway defined by and extending through the partition to allow fluid communication between the lower chamber and the upper chamber;

a plug member extending across the open interior of the lower chamber and sealing the open end of the lower chamber at a position spaced from the partition;

means for initially sealing the passageway to fluid communication therethrough and for subsequently selectively opening the passageway to fluid communication therethrough; and a plunger assembly extending into the upper chamber, said plunger assembly adapted to be reciprocated within the tube-like member and includes means by which to operatively contact and move said plunger assembly in a generally axial direction while permitting descent by force of gravity during analytical test.

2. A cartridge as defined in claim 1 further comprising an optical machine readable code indicative of a predetermined type of analytical test to be conducted with the cartridge and wherein said machine readable code comprises a cover member, a darkened spot on said cover member, and an area defined by the cover within the spot having substantially different light transmissive characteristics than the spot.

3. A cartridge as defined in claim 1 in combination with a machine adapted to receive said cartridge therein and operative to create analytical tests in said cartridge, said machine including means operative in conjunction with said cartridge to detect coagulation-related information by optically sensing a predetermined movement of said plunger assembly within said upper chamber.

4. A cartridge as defined in claim 1 wherein:
said plunger assembly includes said initial sealing and subsequent opening means, and
said initial sealing and subsequent opening means moves out of said passageway upon upward movement of said plunger assembly.

5. A cartridge as defined in claim 1 or 4 wherein:
said plunger assembly comprises a plunger shaft which extends through said upper chamber to an upper end, and
said plunger shaft includes at least one flag member connected to the upper end of the plunger shaft, said flag member located at a position spaced outwardly of the upper end of the tube-like member.

6. A cartridge as defined in claim 5 wherein said means by which to operatively contact and move said plunger assembly includes at least a portion of the flag member.

7. A cartridge as defined in claim 5 further comprising:
shaft stabilizing means extending from the plunger shaft to a position substantially adjacent to the tube-like member for stabilizing the plunger shaft against tilting in at least one transverse direction toward the tube-like member.

8. A cartridge as defined in claim 5 in combination with actuator means for operatively contacting and moving said plug member into contact with said partition after said means operatively opens the passageway to fluid communicating therethrough.

9. A cartridge as defined in claim 5 further comprising:
means extending between the plunger shaft and the tube-like member for operatively resisting axial movement of the plunger shaft relative to the tube-like member when the plunger assembly is initially positioned at a lowermost positions within the upper chamber.

10. A cartridge as defined in claim 9 further comprising:
shaft stabilizing means extending from the plunger shaft to a position substantially adjacent to the tube-like member for stabilizing the plunger shaft against tilting in at least one transverse direction toward the tube-like member.

11. A cartridge as defined in claim 5 in combination with actuator means for operatively interacting with said means by which to contact said plunger assembly to vertically move said plunger shaft to create reciprocating movement of said plunger assembly in said upper chamber.

12. A cartridge as defined in claim 11 wherein said actuator means also operatively contacts and moves said plug member upward toward said partition to reduce the volume of said lower chamber substantially simultaneously with a vertically upward movement of said plunger assembly in said upper chamber.

13. A cartridge as defined in claim 5 wherein said initial sealing and subsequent opening means comprises a resilient member, the resilient member is connected to the lower end of the plunger shaft, and the resilient member is initially positioned within the pasaageway in a resiliently compressed state to establish a fluid-tight seal within the passageway for preventing fluid communicating therethrough.

14. A cartridge as defined in claim 13 wherein said resilient member comprises a disc member having a main body portion and a flange portion extending outward from the main body portion.

15. A cartridge as defined in claim 14 wherein the flange portion defines a plurality of slots extending therethrough.

16. A cartridge as defined in claim 14 wherein the flange portion is annular and extends radially outward from the main body portion.

17. A cartridge as defined in claim 16 wherein the tube-like member in the upper chamber is substantially cylindrical for a predetermined axial distance upward from the partition and is of a diameter greater than the diameter of the annular flange portion to achieve a substantially uniform clearance between the flange portion and the tube-like member over the predetermined axial distance.

18. A cartridge as defined in claim 5 wherein the flag member comprises a contact surface facing toward and spaced from the upper end of the tube-like member, the space between the contact surface of the flag member and the upper end of the tube-like member allowing the insertion of a lifting means therein whereby lifting force is transmitted to the plunger assembly.

19. A cartridge as defined in claim 18 further comprising:
shaft stabilizing means extending from the plunger shaft to a position substantially adjacent the tube-like member for stabilizing the plunger shaft against tilting in at least one transverse direction toward the tube-like member.

20. A cartridge as defined in claim 19 wherein the contact surface of the flag member extends transversely outward from the plunger shaft, and said stabilizing means comprises a projection extending from the shaft member in a transverse direction opposite to that which the contact surface extends, said projection extending from the plunger shaft between its upper and lower ends.

21. A cartridge as defined in claim 20 wherein the projection stabilizes the plunger shaft against tilting upon movement of the lifting means along the contact surface of the flag member.

22. A cartridge as defined in claim 5 wherein said plunger shaft further comprises:
   a cross member extending transversely at a position intermediate the upper and lower ends of the plunger shaft;
   a pair of flag shafts, one flag shaft connected to the cross member and extending upwardly from the cross member at a position adjacent each outer transverse end of the cross member; and
   a pair of said flag members, one flag member connected to upper end of each flag shaft.

23. A cartridge as defined in claim 22 further comprising:
   a vane extending generally in a plane radially outward from the plunger shaft, the vane having a transverse width greater than the transverse width of the plunger shaft.

24. A cartridge as defined in claim 22 further comprising:
   a pair of tabs, one tab extending transversely outward a predetermined distance from each flag shaft toward the tube-like member, said tabs positioned at axial locations on the flag shafts to transversely contact the tube-like member when the plunger assembly is positioned at a lowermost initial position within the upper chamber, the predetermined transverse outward distance to which the tabs extend causing transverse resilient deflection of the flag shafts inward toward one another when the tabs contact the tube-like member.

25. A cartridge as defined in claim 24 further comprising:
   a projection extending from the cross member and terminating at an end edge adapted to contact the tube-like member to operatively prevent tilting of the plunger shaft in one transverse direction relative to the cross member.

26. A cartridge as defined in claim 25 further comprising:
   a vane extending generally in a plane radially outward from the plunger shaft, the vane having a transverse width greater than the transverse width of the plunger shaft.

27. A cartridge as defined in claim 26 wherein the means for initially sealing the passageway comprises a disc member attached to the lower end of the plunger shaft and the disc member further comprises:
   a main disc body portion;
   a flange portion extending outward from the main disc body portion;
   a plurality of slots extending through and defined by the flange portion.

28. A cartridge as defined in claim 27 wherein: the flange portion is annular and extends radially outward from the main disc body portion.

29. A cartridge as defined in claim 28 wherein the tube-like member in the upper chamber is substantially cylindrical for a predetermined axial distance upward from the partition and is of a diameter greater than the diameter of the annular flange portion achieve a substantially uniform clearance between the flange portion and the tube-like member over the predetermined axial distance.

30. A cartridge in which to conduct a coagulation-related analytical test on a sample of liquid blood inserted therein, comprising:
   a tube-like member having an interior surface and defining an open interior extending along an axis therethrough from a lower end to an upper end;
   a partition of the tube-like member located within the open interior and extending inward from the interior surface toward the axis at a position intermediate the upper and lower ends of the tube-like member, said partition generally dividing the open interior into a lower chamber between the partition and the lower end and into an upper chamber between the partition and the upper end;
   a passageway defined by the partition and extending through the partition to allow fluid communication between the lower chamber and the upper chamber;
   a plug member operatively extending across and sealed against the interior surface of the tube-like member within the lower chamber, said plug member adapted to be axially moved along the interior surface of the lower chamber toward the partition;
   a plunger assembly comprising a plunger shaft extending through the upper chamber to an upper end thereof above the upper end of the tube-like member and a disc member connected to the lower end of the plunger shaft;
   the disc member including a main body portion and a flange portion extending outward from an upper end of the main body portion, the flange portion defining a plurality of slots extending through the flange portion, the main body portion initially positioned within the passageway and operative to seal the passageway to fluid communication therethrough;
   said plunger shaft further including means connected to the upper end of the plunger shaft and adapted to be contacted to move the plunger shaft and connected disc member axially upward in the upper chamber, initial upward movement of the disc member from within the passageway opening the passageway to the flow of fluid therethrough;
   said plunger assembly adapted to be reciprocated within the tube-like member in a generally axial direction while permitting descent by force of gravity; and
   a predetermined quantity and type of fluid reagent initially confined in the lower chamber between the partition and the plug member.

31. A cartridge as defined in claim 30 wherein the interior surface of the upper chamber of the tube-like member is concentric about the axis and is of substantially uniform diameter above the partition for a predetermined distance which encompasses a distance in which the disc member moves during the analytical test, and the flange portion extends annularly outwardly from the main body portion to an outermost diameter which is less than the diameter of the interior surface of the upper chamber for the predetermined axial distance above the partition.

32. A cartridge as defined in claim 30 further comprising:
   shaft stabilizing means extending from the plunger shaft to a position substantially adjacent the interior surface of the tube-like member for stabilizing the plunger shaft against tilting in at least one transverse direction toward the interior surface of the tube-like member.

33. A cartridge as defined in claim 30 in combination with actuator means adapted to receive said cartridge and to operatively conduct a coagulation-related analytical test within said cartridge, said actuator means comprising:

means for raising said plunger assembly from its initial position within the upper chamber and releasing said plunger assembly to descend, and thereafter cyclically raising the plunger assembly and releasing it for descent;

means simultaneously operative with said plunger assembly raising means, for moving said lower plug member upward in the lower chamber against the partition to force the fluid reagent into the upper chamber;

means for sensing the descent of the plunger assembly; and means for signalling coagulation upon the sensing of a predetermined condition of descent of the plunger assembly.

34. A cartridge as defined in claim 30 in combination with actuator means adapted to receive said cartridge and to operatively conduct a coagulation-related analytical test within said cartridge, said actuator means comprising:

means for raising said plunger assembly from its initial position within the upper chamber and for thereafter periodically raising said plunger assembly during reciprocative movement of the plunger assembly; and means simultaneously operative with said plunger assembly raising means, for moving said plug member upward in the lower chamber against the partition to force the fluid reagent into the upper chamber substantially simultaneously with the raising of the plunger assembly from its initial position within the upper chamber.

35. A cartridge in combination with actuator means as defined in claim 34, and said actuator means further comprising:

a lift member;

carrying means for carrying said lift member in translational movement between a forward position and a rearward position, said carrying means moving said lift member into contact with said means connected to the upper end of the plunger shaft and adapted to be contacted to move the plunger shaft and disc member axially upward, said carrying means also retaining said lift member for free vertical movement; and slide means operative for contacting said lift member when carried to the forward position and for vertically reciprocating said lift member.

36. A cartridge as defined in claim 30 further comprising:

a cover extending over the upper end of the tube-like member and including at least one hole therein to allow portions of the plunger shaft to extend through the cover; and optically perceptable and machine-readable code on said cover indicative of the cartridge.

37. A cartridge as defined in claim 36 wherein said code comprises a plurality of spots printed on the cover, each spot being substantially opaque, and a hole defined by the cover in the center of at least one spot through which light is transmitted.

38. A cartridge as defined in claim 37 in combination with actuator means adapted to receive said cartridge and to operatively conduct a coagulation-related analytical test with said cartridge, said actuator means comprising means for determining the type of analytical test to be conducted by sensing the code on said cartridge, the code sensing means comprising:

transmitting means directing an identifying light beam onto each spot printed on the cover;

receiving means adapted to receive the identifying light beam from said transmitting means, said receiving means positioned on the opposite side of said cover from said light beam directing means; and the opaque characteristics of each spot substantially interrupting the transmission of each light beam to said receiving means, and the hole in a spot allowing the transmission of light therethrough to said receiving means.

39. A cartridge as defined in claim 30 wherein said plunger shaft further comprises:

a lower shaft portion extending from adjacent the disc member upward to a position intermediate the upper and lower ends of the plunger shaft;

a cross member portion extending transversely from the upper end of the lower shaft portion and terminating at outer edges adjacent to but spaced from the interior surface of the tube-like member;

a pair of flag shafts, one flag shaft connected to the cross member portion and extending upwardly from the cross member portion at a position adjacent each outer edge of the cross member portion; and a pair of flag members, one flag member connected to an upper end of each flag shaft, said means adapted to be contacted to move the plunger shaft axially comprising a surface of each flag member.

40. A cartridge as defined in claim 39 wherein said plunger shaft further comprises:

a tab extending transversely outward a predetermined distance from each flag shaft to an end which faces toward the interior surface of the tube-like member, said tabs positioned at axial positions on the flag shaft intermediate the flag members and the cross member portion to contact ends of the tabs with the interior surface of the tube-like member when the plunger assembly is initially positioned within the upper chamber, the predetermined transverse outward distance to which the ends of the tabs extend causing transverse deflection of the flag shafts inward toward one another when the ends of the tabs transversely contact the interior surface of the tube-like member, the inward deflection of each flag shaft when the ends of the tabs contact the interior surface of the tube-like member being sufficient to develop force for resisting axial movement of the plunger shaft.

41. A cartridge as defined in claim 40 wherein said plunger shaft further comprises:

a projection portion extending outward from the cross member portion and terminating at a forward end edge adjacent to the interior surface of the tube-like member, the forward end edge adapted to contact the interior surface of the tube-like member to operatively prevent substantial tilting of the plunger shaft in a direction transverse with respect to the cross member.

42. A cartridge as defined in claim 41 wherein said flag members extend from the flag shafts substantially in the opposite transverse direction with respect to the cross member from the direction in which the projection portion extends from the cross member portion, and the surface of each flag member which is adapted to be contacted also extends from the flag shafts in the same direction as said flag members extend from said flag shafts, whereby the plunger shaft is substantially stabilized against tilting in a first direction by contact with the surface of the flag members and the flag shafts and in an opposite direction by the contact of the end edge of the projection portion with the interior surface of the tube-like member, and in either transverse direction by contact of outer edges of the cross member portion with the interior surface of the tube-like member.

43. A cartridge as defined in claim 39 wherein said plunger shaft further comprises:
    a vane portion extending generally in the plane of the cross member portion and downwardly from the cross member portion to the lower portion of the plunger shaft, the vane portion having a transverse width greater than the diameter of the lower portion and less than the transverse distance between the outer edges of the cross member portion.

44. A cartridge as defined in claim 43 in combination with actuator means adapted to receive said cartridge and to operatively conduct a coagulation-related analytical test within said cartridge, said actuator means comprising:
    means for raising said plunger assembly from its initial position within the upper chamber and releasing said plunger assembly to descend and thereafter cyclically raising said plunger assembly and releasing it for descent;
    means simultaneously operative with said plunger assembly raising means, for moving said lower plug member upward in the lower chamber against the partition to force the fluid reagent into the upper chamber;
    means directing a light beam into the upper chamber at a position where the cross member and the vane portion interrupt the light beam when the plunger assembly is raised to a predetermined position above its initial position and where transmission of light in the beam occurs after the plunger assembly has descended below the predetermined position;
    means receptive of the light beam for delivering signals in response to the presence or absence of the light beam;
    means responsive to the signals of said light beam receptive means, for measuring the elasped time from the moment when said plunger assembly is released to descend until the moment when transmission of the light beam is reestablished by descent of the plunger assembly beyond the predetermined position; and
    means for signalling coagulation upon the elapsed time for descent of the plunger assembly exceeding a predetermined time period.

45. A cartridge in combination with actuator means as defined in claim 44, wherein:
    said light beam directing and receptive means are positioned on transversely opposite sides of the tube-like member when the cartridge is received in said actuator means, and the light beam extends through said tube-like member and between the pair of flag shafts and above the cross member portion when said plunger assembly descends beyond the predetermined position.

46. A cartridge in which to conduct a coagulation-related analytical test on fluid, comprising:
    a tube-like member having open interior extending generally axially therethrough from an open lower end to an upper end;
    a partition of the tube-like member located within the open interior at a position intermediate the upper and lower ends of the tube-like member, said partition generally dividing the open interior into a lower chamber between the partition and the lower end and into an upper chamber between the partition and the upper end;
    a passageway defined by and extending through the partition to allow fluid communication between the upper and lower chambers;
    a plug member extending across the open interior of the lower chamber and sealing the open end of the lower chamber at a position spaced from the partition;
    a resilient member initially positioned within the passageway in a resiliently sealing state to establish a fluid-tight seal within the passageway for preventing fluid communication therethrough;
    a shaft member connected to the resilient member and extending within the open interior of the tube-like member by which to apply force for removing the resilient member from within the passageway to open the passageway to fluid communication therethrough, and
    said shaft member and resilient member adapted to be reciprocated within the tube-like member in a generally axial direction while permitting descent by force of gravity.

47. A cartridge as defined in claim 46 wherein said plug member is adapted to be axially moved along the interior surface of said lower chamber toward the partition.

48. A cartridge as defned in claim 47 in combination with said actuator means, said actuator means further comprising:
    means operative simultaneously with the application of lifting force to said shaft member to remove said resilient member from the passageway, for moving said plug member in said lower chamber against the partition.

49. A cartridge as defined in claim 46 wherein the shaft member is elongated, one end of the shaft member is connected to the resilient member, the other end of the shaft member extends out of the upper end of the tube-like member, and the other end of the shaft member includes means by which to apply force for moving the shaft member and the connected resilient member.

50. A cartridge as defined in claim 49 wherein said means connected to the other end of the shaft member comprises a flag member connected to the other end of the shaft.

51. A cartridge as defined in claim 50 wherein the flag member comprises a contact surface facing toward and spaced from the upper end of the tube-like member, the space between the contact surface of the flag member and the upper end of the tube-like member allowing the insertion of a lifting means therein whereby to transmit forces to the flag member.

52. A cartridge as defined in claim 51 further comprising shaft stabilizing means extending from the shaft member to a position substantially adjacent the tube-like member for stabilizing the shaft member against substantial tilting toward the tube-like member.

53. A cartridge as defined in claim 52 wherein the contact surface extends transversely outward from the shaft member, and said stabilizing means comprises a projection extending from the shaft member in a transverse direction opposite to that which the contact surface extends, said projection positioned on the plunger shaft between the flag member and the resilient member.

54. A cartridge as defined in claim 53 wherein said shaft stabilizing means stabilizes the shaft member against tilting upon movement of the lifting means between the contact surface of the flag member and the upper end of the tube-like member.

55. A cartridge as defined in claims 52 or 54 wherein the resilient member connected to the lower end of the shaft member comprises:
 a main body portion; and
 a flange portion extending outward from the main body portion.

56. A cartridge as defined in claim 55 wherein the flange portion of the resilient member further defines a plurality of slots extending therethrough.

57. A cartridge as defined in claim 56 wherein the flange portion is annular and extends radially outward from the main body portion.

58. A cartridge as defined in claim 57 wherein the tube-like member in the upper chamber is substantially cylindrical for a predetermined axial distance from the partition and is of a diameter greater than the diameter of the annular flange portion to achieve a substantially uniform clearance between the flange portion and the tube-like member over the predetermined axial distance.

59. A cartridge as defined in claim 56 in combination with actuator means adapted to receive said cartridge and to operatively conduct a coagulation-related analytical test within said cartridge, said actuator means comprising:
 lifting means for contacting said contact surface to raise the shaft member and connected resilient member from the initial position and to release the assembly of the shaft member and the resilient member for descent, and thereafter cyclically raising the assembly and releasing it for descent; and
 means for sensing the descent of the assembly and for determining coagultion conditions from the sensed descent of the assembly.

60. A cartridge as defined in claim 59 in combination with said actuator means, said means for sensing the descent comprising optical means for sensing a predetermined condition of movement of the assembly.

61. A cartridge as defined in claim 60
 a plug member extending across the open interior of one of said chambers and sealing the open end of said chamber at a wherein said plug member is adapted to be axially moved along the interior surface of said lower chamber toward the partition.

62. A cartridge as defined in claim 61 in combination with said actuator means, said actuator means further comprising:
 means operative simultaneously with the application of lifting force to said shaft member to remove said resilient member from the passageway, for moving said plug member in said lower chamber against the partition.

63. A cartridge in which to conduct a coagulation related analytical test on fluid, comprising:
 a tube-like member having an open interior extending generally axially therethrough from a open lower end to an upepr end; a partition of the tube-like member located within the open interior at a position intermediate the upper and lower ends of the tube-like member, said partition generally dividing the open interior into a lower chamber between the partition and the lower end and into an upper chamber between the partition and the upper end;
 a means extending across the open interior of the lower chamber and initially sealing the open end of the lower chamber at a position spaced from the partition; means for intitially sealing the passageway to fluid communication therethrough and for subsequently selectively opening the passageway to fluid communication therethrough;
 a plunger assembly having an elongated plunger shaft extending into the upper chamber;
 retarding means connected to one end of the plunger shaft within the chamber and operative for interacting with a fluid in the upper chamber and retarding movement of the plunger shaft through the fluid in a predetermined relation to the viscosity of the fluid; and
 a contact member connected to the other end of the plunger shaft and located exteriorly of the upper end of the tube-like member, said contact member defining a contact surface facing toward the upper end of the tube-like member, the contact surface spaced from the upper end of the tube-like member a predetermined distance to allow the insertion of lifting means therein to allow lifting of the plunger assembly during the analytical test.

64. A cartridge as defined in claim 63 in combination with actuator means adapted to receive said cartridge and to operatively conduct a coagulation-related analytical test within said cartridge, said actuator means comprising:
 lifting means for contacting said contact surface to raise the shaft member and the retarding means and to release the assembly of the shaft member and the retarding means for descent through the fluid, and thereafter cyclically raising the assembly and releasing it for descent; and
 means for sensing the descent of the assembly and for determining coagulation conditions from the sensed descent of the assembly.

65. A cartridge as defined in claim 64 in combination with said actuator means, said means for sensing the descent comprising optical means for sensing predetermined conditions for movement of the assembly.

66. A cartridge as defined in claim 63 further comprising shaft stabilizing means extending from the shaft member to a position substantially adjacent the tube-like member for stabilizing the shaft member against substantial tilting toward the tube-like member.

67. A cartridge as defined in claim 66 wherein the contact surface extends transversely outward from the shaft member, and said stabilizing means comprises a projection extending from the shaft member in a transverse direction opposite to that which the contact surface extends, said projection positioned on the plunger shaft between the contact member and the retarding means.

68. A cartridge as defined in claim 67 wherein said shaft stabilizing means stabilizes the shaft member against tilting upon movement of the lifting means between the contact surface of the contact member and the one upper end of the tube-like member.

* * * * *